US012582337B2

(12) United States Patent
Campbell et al.

(10) Patent No.: US 12,582,337 B2
(45) Date of Patent: Mar. 24, 2026

(54) SOLID-STATE SUBSTRATE-INTEGRATED REFERENCE ELECTRODE AND COUNTER ELECTRODE

(71) Applicant: Biolinq Incorporated, San Diego, CA (US)

(72) Inventors: Alan Campbell, San Diego, CA (US); Jennifer Ruth Walters Fuchs, Carlsbad, CA (US); Joshua Ray Windmiller, San Diego, CA (US)

(73) Assignee: Biolinq Incorporated, San Diego, CA (US)

( * ) Notice: Subject to any disclaimer, the term of this patent is extended or adjusted under 35 U.S.C. 154(b) by 518 days.

(21) Appl. No.: 17/542,273

(22) Filed: Dec. 3, 2021

(65) Prior Publication Data

US 2022/0175278 A1 Jun. 9, 2022

Related U.S. Application Data

(60) Provisional application No. 63/121,223, filed on Dec. 3, 2020.

(51) Int. Cl.
*A61B 5/1468* (2006.01)
*A61B 5/145* (2006.01)
(Continued)

(52) U.S. Cl.
CPC ........ *A61B 5/1468* (2013.01); *A61B 5/14546* (2013.01); *C25D 5/02* (2013.01);
(Continued)

(58) Field of Classification Search
CPC ............. G01N 27/403; G01N 27/3275; G01N 27/327; G01N 27/3271; G01N 27/3272;
(Continued)

(56) References Cited

U.S. PATENT DOCUMENTS 3,964,482 A 6/1976 Gerstel et al.
4,305,401 A 12/1981 Reissmueller et al.
(Continued)

FOREIGN PATENT DOCUMENTS

CN 101915794 A 12/2010
CN 110558993 A 12/2019
(Continued)

OTHER PUBLICATIONS

Abbot press release (2020). "New late-breaking data show use of abbott's Freestyle® Libre System significantly reduces HBA1C levels in people with type 2 diabetes using insulin or not," 3 pages.
(Continued)

*Primary Examiner* — Gurpreet Kaur
(74) *Attorney, Agent, or Firm* — Cooley LLP

(57) ABSTRACT

Aspects are directed to a reference electrode integrated on a surface of a substrate to facilitate functionalization of a working electrode. The reference electrode is used in the electrochemical deposition or electrodeposition of one or more functional layers on a working electrode. The working electrode may be a sensing element of an analyte-selective sensor. Additional aspects of the current subject matter are directed to a counter electrode integrated on a surface of a substrate.

27 Claims, 4 Drawing Sheets

(51) Int. Cl.

| | |
|---|---|
| *C25D 5/02* | (2006.01) |
| *C25D 17/12* | (2006.01) |
| *G01N 27/403* | (2006.01) |
| *C25D 21/00* | (2006.01) |

(52) U.S. Cl.
CPC ........ *C25D 17/12* (2013.01); *A61B 2562/125* (2013.01); *A61B 2562/164* (2013.01); *A61B 2562/227* (2013.01); *C25D 21/00* (2013.01)

(58) Field of Classification Search
CPC ........ A61B 2562/125; A61B 2562/164; A61B 2562/227; A61B 5/14514; A61B 5/14546; A61B 5/1468; A61B 5/262
See application file for complete search history.

(56) References Cited

U.S. PATENT DOCUMENTS

| | | | |
|---|---|---|---|
| 4,323,996 A | 4/1982 | Ganter |
| 4,407,295 A | 10/1983 | Steuer et al. |
| 4,450,842 A | 5/1984 | Zick et al. |
| 4,756,807 A | 7/1988 | Meyer et al. |
| 4,908,117 A | 3/1990 | Kinlen et al. |
| 5,131,390 A | 7/1992 | Sakaguchi et al. |
| 5,166,063 A | 11/1992 | Johnson |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 6,036,055 A | 3/2000 | Mogadam et al. |
| 6,132,449 A | 10/2000 | Lum et al. |
| 6,139,718 A | 10/2000 | Kurnik et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,471,903 B2 | 10/2002 | Sherman et al. |
| 6,603,987 B2 | 8/2003 | Whitson |
| 6,793,789 B2 | 9/2004 | Choi et al. |
| 6,814,845 B2 | 11/2004 | Wilson et al. |
| 6,862,466 B2 | 3/2005 | Ackerman |
| 6,908,453 B2 | 6/2005 | Fleming et al. |
| 7,097,776 B2 | 8/2006 | Govinda Raju |
| 7,132,054 B1 | 11/2006 | Kravitz et al. |
| 7,169,284 B1 | 1/2007 | Jiang et al. |
| 7,220,550 B2 | 5/2007 | Keen |
| 7,262,068 B2 | 8/2007 | Roy et al. |
| 7,343,188 B2 | 3/2008 | Sohrab |
| 7,344,499 B1 | 3/2008 | Prausnitz et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,473,244 B2 | 1/2009 | Frazier et al. |
| 7,493,232 B1 | 2/2009 | Surina |
| 7,837,654 B2 | 11/2010 | Shumate et al. |
| 7,949,382 B2 | 5/2011 | Jina |
| 8,005,526 B2 | 8/2011 | Martin et al. |
| 8,022,292 B2 | 9/2011 | Arianpour et al. |
| 8,088,321 B2 | 1/2012 | Ferguson et al. |
| 8,094,009 B2 | 1/2012 | Allen et al. |
| 8,108,023 B2 | 1/2012 | Mir et al. |
| 8,125,331 B2 | 2/2012 | Allen et al. |
| 8,160,665 B2 | 4/2012 | Mischler et al. |
| 8,280,476 B2 | 10/2012 | Jina |
| 8,284,046 B2 | 10/2012 | Allen et al. |
| 8,574,165 B2 | 11/2013 | Marsh |
| 8,660,628 B2 | 2/2014 | Wang et al. |
| 8,798,799 B2 | 8/2014 | Deo et al. |
| 9,008,745 B2 | 4/2015 | Pushpala et al. |
| 9,182,368 B2 | 11/2015 | Pushpala et al. |
| 9,387,000 B2 | 7/2016 | Corrie et al. |
| 9,551,698 B2 | 1/2017 | Huys et al. |
| 9,737,247 B2 | 8/2017 | Wang et al. |
| 9,743,870 B2 | 8/2017 | Wang et al. |
| 9,933,387 B1 | 4/2018 | McCanna et al. |
| 9,958,409 B2 | 5/2018 | Gerber et al. |
| 10,092,207 B1 | 10/2018 | Windmiller |
| 10,136,846 B2 | 11/2018 | Wang et al. |
| 10,173,042 B2 | 1/2019 | Pushpala et al. |
| 10,231,654 B2 | 3/2019 | Peyser et al. |
| 10,376,188 B2 | 8/2019 | Simpson et al. |
| 10,426,383 B2 | 10/2019 | Huang et al. |
| 10,492,708 B1 | 12/2019 | Windmiller |
| D875,254 S | 2/2020 | Cooke et al. |
| 10,549,080 B2 | 2/2020 | Pushpala et al. |
| 10,820,860 B2 | 11/2020 | Pushpala et al. |
| 11,035,872 B2 | 6/2021 | Boutelle et al. |
| 11,045,142 B1 | 6/2021 | Windmiller et al. |
| 11,123,532 B2 | 9/2021 | Pushpala et al. |
| 11,197,985 B2 | 12/2021 | Pushpala et al. |
| 11,272,866 B2 | 3/2022 | Pushpala et al. |
| 11,272,885 B2 | 3/2022 | Pushpala et al. |
| 11,291,390 B2 | 4/2022 | Pushpala et al. |
| 11,359,300 B1 | 6/2022 | Beer et al. |
| 11,478,194 B2 | 10/2022 | Windmiller et al. |
| 11,654,270 B2 | 5/2023 | Mansfield, III et al. |
| D988,160 S | 6/2023 | Morelock |
| 11,672,965 B2 | 6/2023 | Mansfield, III et al. |
| D996,999 S | 8/2023 | Morelock |
| D1,012,744 S | 1/2024 | Morelock |
| 11,857,344 B2 | 1/2024 | Windmiller et al. |
| 11,872,055 B2 | 1/2024 | Tangney et al. |
| D1,013,544 S | 2/2024 | Morelock |
| 11,904,127 B2 | 2/2024 | Mansfield et al. |
| 11,963,796 B1 | 4/2024 | Windmiller et al. |
| 11,986,614 B2 | 5/2024 | Mansfield et al. |
| 12,011,294 B2 | 6/2024 | Campbell et al. |
| D1,033,641 S | 7/2024 | Morelock |
| D1,035,004 S | 7/2024 | Morelock |
| D1,038,794 S | 8/2024 | Morelock |
| 12,070,307 B2 | 8/2024 | Ebejer et al. |
| 12,070,313 B2 | 8/2024 | Fuchs et al. |
| 12,109,032 B1 | 10/2024 | Windmiller et al. |
| D1,051,745 S | 11/2024 | Morelock |
| D1,057,153 S | 1/2025 | Morelock |
| D1,068,516 S | 4/2025 | Morelock |
| 12,279,888 B2 | 4/2025 | Campbell et al. |
| 12,285,271 B2 | 4/2025 | Campbell et al. |
| 12,336,816 B2 | 6/2025 | Campbell et al. |
| D1,083,640 S | 7/2025 | Morelock |
| D1,083,977 S | 7/2025 | Morelock |
| 2003/0104119 A1 | 6/2003 | Wilson et al. |
| 2003/0225360 A1 | 12/2003 | Eppstein et al. |
| 2005/0109622 A1 | 5/2005 | Peumans et al. |
| 2006/0015061 A1 | 1/2006 | Kuo et al. |
| 2006/0264716 A1 | 11/2006 | Zander |
| 2007/0170054 A2 | 7/2007 | Wilsey |
| 2007/0213044 A1 | 9/2007 | Steingart et al. |
| 2007/0282246 A1 | 12/2007 | Henley |
| 2008/0097352 A1 | 4/2008 | Beck et al. |
| 2008/0154107 A1 | 6/2008 | Jina |
| 2008/0234562 A1 | 9/2008 | Jina |
| 2009/0069651 A1 | 3/2009 | Zimmermann et al. |
| 2009/0069697 A1 | 3/2009 | Frazier et al. |
| 2009/0088652 A1 | 4/2009 | Tremblay |
| 2009/0131778 A1 | 5/2009 | Jina et al. |
| 2009/0143761 A1 | 6/2009 | Cantor et al. |
| 2009/0259118 A1 | 10/2009 | Feldman et al. |
| 2009/0273356 A1 | 11/2009 | Pampin et al. |
| 2010/0049021 A1 | 2/2010 | Jina et al. |
| 2010/0052897 A1 | 3/2010 | Allen et al. |
| 2010/0056873 A1 | 3/2010 | Allen et al. |
| 2010/0200538 A1 | 8/2010 | Petisce et al. |
| 2010/0286803 A1 | 11/2010 | Tillotson et al. |
| 2011/0077490 A1* | 3/2011 | Simpson ............ A61B 5/14503 600/345 |
| 2011/0087315 A1 | 4/2011 | Richardson-Burns et al. |
| 2011/0105871 A1 | 5/2011 | Zimmermann et al. |
| 2011/0175074 A1 | 7/2011 | Osterbacka et al. |
| 2011/0237925 A1 | 9/2011 | Yue et al. |
| 2011/0301677 A1 | 12/2011 | Hendricks et al. |
| 2012/0067734 A1 | 3/2012 | Wang et al. |
| 2012/0172692 A1 | 7/2012 | Tamada et al. |

(56) References Cited

U.S. PATENT DOCUMENTS

| 2012/0323097 | A9 | 12/2012 | Chowdhury |
|---|---|---|---|
| 2013/0053660 | A1 | 2/2013 | Shieh |
| 2013/0065257 | A1 | 3/2013 | Wang et al. |
| 2013/0144131 | A1 | 6/2013 | Wang et al. |
| 2013/0225956 | A1 | 8/2013 | Huang et al. |
| 2013/0245412 | A1 | 9/2013 | Rong et al. |
| 2013/0281808 | A1 | 10/2013 | Shieh |
| 2014/0259652 | A1 | 9/2014 | Pushpala et al. |
| 2014/0275897 | A1 | 9/2014 | Pushpala et al. |
| 2014/0336487 | A1 | 11/2014 | Wang et al. |
| 2014/0357964 | A1 | 12/2014 | Wisniewski et al. |
| 2015/0276758 | A1 | 10/2015 | Addisu |
| 2015/0313527 | A1 | 11/2015 | Renlund |
| 2016/0029937 | A1 | 2/2016 | Sia et al. |
| 2016/0058342 | A1 | 3/2016 | Maiz-Aguinaga et al. |
| 2016/0095541 | A1 | 4/2016 | Wang et al. |
| 2016/0256091 | A1 | 9/2016 | Cho et al. |
| 2016/0270704 | A1 | 9/2016 | Deturk |
| 2016/0296149 | A1 | 10/2016 | Polsky et al. |
| 2016/0302687 | A1 | 10/2016 | Lee et al. |
| 2016/0370377 | A1 | 12/2016 | Ahmad |
| 2017/0007813 | A1 | 1/2017 | Negi et al. |
| 2017/0251960 | A1 | 9/2017 | Crouther et al. |
| 2018/0116572 | A1 | 5/2018 | Simpson et al. |
| 2019/0125223 | A1 | 5/2019 | Wang et al. |
| 2019/0224712 | A1 | 7/2019 | Petisce et al. |
| 2019/0309433 | A1 | 10/2019 | Sattayasamitsathit et al. |
| 2019/0310219 | A1 | 10/2019 | Boock |
| 2020/0085341 | A1 | 3/2020 | Windmiller |
| 2020/0101286 | A1 | 4/2020 | Windmiller et al. |
| 2020/0104733 | A1 | 4/2020 | Bart |
| 2020/0121902 | A1 | 4/2020 | Pushpala et al. |
| 2020/0214566 | A1 | 7/2020 | Allen et al. |
| 2020/0254240 | A1 | 8/2020 | Windmiller et al. |
| 2020/0297997 | A1 | 9/2020 | Windmiller et al. |
| 2021/0100504 | A1 | 4/2021 | Pushpala et al. |
| 2021/0187286 | A1 | 6/2021 | Windmiller et al. |
| 2021/0369155 | A1* | 12/2021 | Feldman ............ A61B 5/14865 |
| 2021/0386338 | A1 | 12/2021 | Zhang et al. |
| 2021/0393201 | A1 | 12/2021 | Morelock et al. |
| 2022/0031209 | A1 | 2/2022 | Windmiller et al. |
| 2022/0031244 | A1 | 2/2022 | Windmiller et al. |
| 2022/0054813 | A1 | 2/2022 | Pushpala et al. |
| 2022/0054814 | A1 | 2/2022 | Pushpala et al. |
| 2022/0151518 | A1 | 5/2022 | Pushpala et al. |
| 2022/0151519 | A1 | 5/2022 | Pushpala et al. |
| 2022/0151558 | A1 | 5/2022 | Pushpala et al. |
| 2022/0175279 | A1 | 6/2022 | Pushpala et al. |
| 2022/0233107 | A1 | 7/2022 | Pushpala et al. |
| 2022/0370011 | A1 | 11/2022 | Windmiller et al. |
| 2023/0074798 | A1 | 3/2023 | Tangney et al. |
| 2023/0094419 | A1 | 3/2023 | Mansfield, III et al. |
| 2023/0099617 | A1 | 3/2023 | Mansfield, III et al. |
| 2023/0137258 | A1 | 5/2023 | Windmiller |
| 2023/0190147 | A1 | 6/2023 | Campbell et al. |
| 2023/0256220 | A1 | 8/2023 | Mansfield, III et al. |
| 2023/0301552 | A1 | 9/2023 | Mallires et al. |
| 2023/0310823 | A1 | 10/2023 | Mansfield, III et al. |
| 2023/0414102 | A1 | 12/2023 | Allen et al. |
| 2024/0008777 | A1 | 1/2024 | Fuchs et al. |
| 2024/0081740 | A1 | 3/2024 | Windmiller et al. |
| 2024/0164719 | A1 | 5/2024 | Campbell et al. |
| 2024/0252115 | A1 | 8/2024 | Tangney et al. |
| 2024/0315614 | A1 | 9/2024 | Campbell et al. |
| 2024/0341636 | A1 | 10/2024 | Yang et al. |
| 2024/0366125 | A1 | 11/2024 | Alonso-Soski et al. |
| 2024/0382157 | A1 | 11/2024 | Windmiller et al. |
| 2024/0408366 | A1 | 12/2024 | Mansfield et al. |
| 2024/0423526 | A1 | 12/2024 | Windmiller et al. |
| 2025/0000395 | A1 | 1/2025 | Brister et al. |
| 2025/0049397 | A1 | 2/2025 | Campbell et al. |
| 2025/0213859 | A1 | 7/2025 | Windmiller et al. |

FOREIGN PATENT DOCUMENTS

| EP | 4048152 | B1 | 12/2023 |
|---|---|---|---|
| KR | 10-2016-0108111 | A | 9/2016 |
| WO | WO-89/006855 | A1 | 7/1989 |
| WO | WO-2006/093422 | A1 | 9/2006 |
| WO | WO-2009/034313 | A2 | 3/2009 |
| WO | WO-2009/034313 | A3 | 3/2009 |
| WO | WO-2009/064164 | A2 | 5/2009 |
| WO | WO-2009/064164 | A3 | 5/2009 |
| WO | WO-2010/120364 | A2 | 10/2010 |
| WO | WO-2010/120364 | A3 | 10/2010 |
| WO | WO-2012/020332 | A2 | 2/2012 |
| WO | WO-2012/020332 | A3 | 2/2012 |
| WO | WO-2013/058879 | A2 | 4/2013 |
| WO | WO-2013/058879 | A3 | 4/2013 |
| WO | WO-2015/073459 | A1 | 5/2015 |
| WO | WO-2016189301 | A1 | 12/2016 |
| WO | WO-2018071265 | A1 | 4/2018 |
| WO | WO-2018/164886 | A1 | 9/2018 |
| WO | WO-2020117918 | A1 | 6/2020 |
| WO | WO-2021257624 | A1 | 12/2021 |
| WO | WO-2022010812 | A1 | 1/2022 |
| WO | WO-2022026764 | A1 | 2/2022 |
| WO | WO-2022120239 | A1 | 6/2022 |
| WO | WO-2022240700 | A1 | 11/2022 |
| WO | WO-2023055755 | A1 | 4/2023 |
| WO | WO-2023064877 | A1 | 4/2023 |
| WO | WO-2023133468 | A1 | 7/2023 |
| WO | WO-2023229662 | A2 | 11/2023 |
| WO | WO-2024010827 | A1 | 1/2024 |
| WO | WO-2024163950 | A2 | 8/2024 |
| WO | WO-2024238798 | A1 | 11/2024 |
| WO | WO-2025144429 | A2 | 7/2025 |

OTHER PUBLICATIONS

American Diabetes Association® Press Release (2020). "American Diabetes Association® Applauds policymakers' Focus on Addressing High Costs of Insulin for Seven Million Americans," 4 pages.

Ammam, M. (2012). "Electrophoretic deposition under modulated electric fields: A review," RSC Advances 2:7633-7646.

Bantle, J.P. et al. (1997). "Glucose measurement in patients with diabetes mellitus with dermal interstitial fluid," J. Lab. Clin. Med. 130:436-441.

Beckles, G.L. et al. (2016). "Disparities in the prevalence of diagnosed diabetes—United States, 1999-2002 and 2011-2014," MMWR 65:1265-1269.

Cao, J. et al. (2017). "Validation of capillary blood analysis and capillary testing mode on the epoc Point of Care system," Pract. Lab. Med. 9:24-27.

Castle, J.R. et al. (2012). "The accuracy benefit of multiple amperometric glucose sensors in people with type 1 diabetes," Diabetes Care 35:706-710.

Chou, J.-C. et al. (2013). 'Fabrication and Investigation of Arrayed Glucose Biosensor Based on Microfluidic Framework,' IEEE Sensors Journal 13:4180-4187.

Dexcom (2020). Analyst Day Presentation, 19 total pages.

Dexcom (2020). Analyst Day Presentation, 27 total pages.

Diabetes Care (2021). "7. Diabetes Technology: Standards of Medical Care in Diabetes—2021," Diabetes Care 44(Supplement 1):S85-S99.

Extended European Search Report mailed on Feb. 25, 2020, for EP Application No. 17 860 1884.0, filed on Oct. 5, 2017, 7 pages.

Fang, M. et al. (2021). "Trends in Diabetes Treatment and Control in U.S. Adults, 1999-2018," N. Engl. Med. 384:2219-2228.

Final Office Action mailed on Feb. 15, 2022, for U.S. Appl. No. 16/334,022, filed Mar. 17, 2019, 11 pages.

French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.

Grady, M. et al. (2017). "Examining the Impact of a Novel Blood Glucose Monitor With Color Range Indicator on Decision-Making

(56) References Cited

OTHER PUBLICATIONS in Patients With Type 1 and Type 2 Diabetes and its Association With Patient Numeracy Level," JMIR Diabetes 2:e24.

Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.

Groenendaal, W. et al. (2008). "Modeling Glucose and Water Dynamics in Human Skin," Diab. Tech. Therap. 10:283-293.

International Search Report mailed on Jan. 5, 2018, for PCT Application No. PCT/US2017/055314, filed on Oct. 5, 2017, 2 pages.

International Search Report mailed on Feb. 14, 2022, for PCT Application No. PCT/US2021/061903, filed on Dec. 3, 2021, 2 pages.

Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.

Karter, A.J. et al. (2021). "Association of Real-time Continuous Glucose Monitoring With Glycemic Control and Acute Metabolic Events Among Patients With Insulin-Treated Diabetes," JAMA 325:2273-2284.

Kassim, A. et al. (2001). "Effect of reactor configuration and temperature on Electropolymerization of Sodium Camphorsulfonate-Doped Polypyrrole," Malaysian Journal of Analytical Sciences 7:25-27.

Mangold, K.M. (2001). "Reference electrodes based on conducting polymer bilayers," Synthetic Metals 119:345-346.

Martens, T. et al. (2021). "Effect of Continuous Glucose Monitoring on Glycemic Control in Patients with Type 2 Diabetes Treated with Basal Insulin A Randomized Clinical Trial," JAMA 325:2262-2272.

McClatchey, P.M. et al. (2019). "Fibrotic Encapsulation Is the Dominant Source of Continuous Glucose Monitor Delays," Diabetes 68:1892-1901.

Neerken, S. et al. (2004). "Characterization of age-related effects in human skin: A comparative study that applies confocal laser scanning microscopy and optical coherence tomography," J. Biomed. Optics 9:274-281.

Non-Final Office Action mailed on Apr. 16, 2019, for U.S. Appl. No. 16/152,372, filed Oct. 4, 2018, 11 pages.

Non-Final Office Action mailed on Jun. 23, 2021, for U.S. Appl. No. 16/666,259, filed Oct. 28, 2019, 12 pages.

Non-Final Office Action mailed on Jul. 1, 2021, for U.S. Appl. No. 16/334,022, filed Mar. 17, 2019, 11 pages.

Notice of Allowance mailed on Aug. 28, 2018, for U.S. Appl. No. 15/590,105, filed May 9, 2017, 8 pages.

Notice of Allowance mailed on Sep. 9, 2019, for U.S. Appl. No. 16/152,372, filed Oct. 4, 2018, 7 pages.

Notice of Allowance mailed on Jan. 28, 2022, for U.S. Appl. No. 16/666,259, filed Oct. 28, 2019, 8 pages.

Notice of Allowance mailed on Apr. 22, 2022, for U.S. Appl. No. 16/666,259, filed Oct. 28, 2019, 8 pages.

Polonsky, W.H. et al. (2011). "A survey of blood glucose monitoring in patients with type 2 diabetes: Are recommendations from health care professionals being followed?" Curr. Med. Res. & Opinion 27:31-37.

Rigla, M. et al. (2018). "Human Subcutaneous Tissue Response to Glucose Sensors: Macrophages Accumulation Impact on Sensor Accuracy," Diabetes Technology & Therapeutics 20:296-302.

Sheikh, Z. et al. (2015). "Macrophages, Foreign Body Giant Cells and Their Response to Implantable Biomaterials," Materials 8:5671-5701.

Shi, T. et al. (2016). "Modeling and Measurement of Correlation between Blood and Interstitial Glucose Changes," J. Diab. Res. vol. 2016, 9 pages.

Waltman, R.J. et al. (1986). "Electrically conducting polymers: a review of the electropolymerization reaction, of the effects of chemical structure on polymer film properties, and of applications towards technology," Canadian Journal of Chemistry 64:76-95.

Written Opinion of the International Searching Authority mailed on Jan. 5, 2018, for PCT Application No. PCT/US2017/055314, filed on Oct. 5, 2017, 9 pages.

Written Opinion of the International Searching Authority mailed on Feb. 14, 2022, for PCT Application No. PCT/US2021/061903, filed on Dec. 3, 2021, 9 pages.

Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. 8 pages. doi: 10.7759/cureus.11195.

Allen et al., "Continuous glucose monitoring counseling improves physical activity behaviors of individuals with type 2 diabetes: A randomized clinical trial" Diabetes Res Clin Pract. Jun. 2008; 80(3): 371-379. doi:10.1016/j.diabres.2008.01.006.

Barrett et al., "Risk for Newly Diagnosed Diabetes 30 Days After SARS-CoV-2 Infection Among Persons Aged 18 Years—United States, Mar. 1, 2020-Jun. 28, 2021" MMWR Morb Mortal Wkly Rep. Jan. 14, 2022; 71(2):59-65. doi: 10.15585/mmwr.mm7102e2.

Centers for Disease Control, "National Diabetes Statistics Report 2020 Estimates of Diabetes and Its Burden in the United States" (2020) 32 pages.

Deore, B., et al., "Potential-induced enantioselective uptake of amino acid into molecularly imprinted overoxidized polypyrrole", Anal. Chem. (2000) 72:3989-3994.

Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.

Ehrhardt et al, "Behavior Modification in Prediabetes and Diabetes: Potential Use of Real-Time Continuous Glucose Monitoring" Journal of Diabetes Science and Technology Mar. 2019; 13(2):271-275.

Ehrhardt et al., "Continuous Glucose Monitoring As a Behavior Modification Tool" Clin Diabetes. Apr. 2020; 38(2):126-131. doi: 10.2337/cd19-0037.

Ehrhardt et al, "The Effect of Real-Time Continuous Glucose Monitoring on Glycemic Control in Patients with Type 2 Diabetes Mellitus" Journal of Diabetes Science and Technology May 2011; 5(3):668-675.

Final Office Action mailed on Mar. 23, 2023, for U.S. Appl. No. 16/334,022, filed Mar. 17, 2019, 14 pages.

Fonda et al., "The Cost-Effectiveness of Real-Time Continuous Glucose Monitoring (RT-CGM) in Type 2 Diabetes" Journal of Diabetes Science and Technology (2016) 10(4):898-904.

Han et al., "The End of the Road for the YSI 2300 Analyzer: Where Do We Go Now?" Journal of Diabetes Science and Technology (2020) 14(3):595-600.

Han et al., "The YSI 2300 Analyzer Replacement Meeting Report" Journal of Diabetes Science and Technology (2020) 14(3):679-686.

Non-Final Office Action mailed on Sep. 15, 2022, for U.S. Appl. No. 16/334,022, filed Mar. 17, 2019, 13 pages.

Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.

Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.

Vigersky et al., "Short- and Long-Term Effects of Real-Time Continuous Glucose Monitoring in Patients with Type 2 Diabetes" Diabetes Care Jan. 2012; 35:32-38.

Wolicki et al., "Epidemiology and Prevention of Vaccine-Preventable Diseases: Chapter 6: Vaccine Administration" Centers for Disease Control and Prevention (2021) 17 pages.

World Health Organization, "Diabetes", Sep. 16, 2022, 5 pages.

Young et al., "Glucose Self-monitoring in Non-Insulin-Treated Patients With Type 2 Diabetes in Primary Care Settings: A Randomized Trial" JAMA Intern Med. Jul. 2017; 177(7):920-929.

American Diabetes Association, "Diabetes and Emotional Health: A Practical Guide for Health Professionals Supporting Adults with Type 1 and Type 2 Diabetes" U.S. Edition (2021), 214 pages.

(56)                    References Cited

OTHER PUBLICATIONS

American Diabetes Association Professional Practice Committee, "6. Glycemic Goals and Hypoglycemia: Standards of Care in Diabetes—2024" Diabetes Care Jan. 1, 2024; 47(Suppl 1):S111-S125.

American Diabetes Association Professional Practice Committee, "7. Diabetes Technology: Standards of Medical Care in Diabetes—2022" Diabetes Care Jan. 1, 2022; 45(Suppl 1):S97-S112.

Centers for Disease Control, "National Diabetes Statistics Report" May 2024, 16 pages.

Chen et al., "All-Solid-State Conductive Polymer Miniaturized Reference Electrode" Japanese Journal of Applied Physics (2009) 48:111501-1-111501-6, 7 pages.

Diabetes Control and Complications Trial Research Group, "The effect of intensive treatment of diabetes on the development and progression of long-term complications in insulin-dependent diabetes mellitus" N Engl J Med Sep. 30, 1993; 329(14):977-986.

Elsayed et al., "2. Classification and Diagnosis of Diabetes: Standards of Care in Diabetes—2023" Diabetes Care Jan. 1, 2023; 46(Suppl 1):S19-S40.

Extended European Search Report for European Application No. 21901579.9 mailed Oct. 4, 2024, 10 pages.

Mendes-Soares et al., "Assessment of a Personalized Approach to Predicting Postprandial Glycemic Responses to Food Among Individuals Without Diabetes" JAMA Network Open Feb. 1, 2019; 2(2):e188102. 13 pages.

Miller et al., "Hypoglycemia in patients with type 2 diabetes mellitus" Arch Intern Med Jul. 9, 2001; 161(13):1653-1659.

Newton et al., "Diabetic ketoacidosis in type 1 and type 2 diabetes mellitus: clinical and biochemical differences" Arch Intern Med Sep. 27, 2004; 164(17):1925-1931.

Non-Final Office Action for U.S. Appl. No. 16/334,022 dated Oct. 11, 2023, 12 pages.

Segel et al., "Hypoglycemia-associated autonomic failure in advanced type 2 diabetes" Diabetes Mar. 2002; 51(3):724-733.

Shivers et al., "Turn it off!: diabetes device alarm fatigue considerations for the present and the future" J Diabetes Sci Technol May 1, 2013; 7(3):789-794.

Tanenbaum et al., "Diabetes Device Use in Adults With Type 1 Diabetes: Barriers to Uptake and Potential Intervention Targets" Diabetes Care Feb. 2017; 40(2):181-187.

UK Prospective Diabetes Study (UKPDS) Group, "Intensive blood-glucose control with sulphonylureas or insulin compared with conventional treatment and risk of complications in patients with type 2 diabetes (UKPDS 33)" Lancet Sep. 12, 1998; 352(9131):837-853.

Yoon, Y. et al. (2013). "Fabrication of a Microneedle/CNT Hierarchical Micro/Nano Surface Electrochemical Sensor and Its In-Vitro Glucose Sensing Characterization," Sensors 13:16672-16681.

Battelino et al., "Continuous glucose monitoring and metrics for clinical trials: an international consensus statement" Lancet Diabetes Endocrinol (2023) 11:42-57.

Clutter et al., "Epinephrine plasma metabolic clearance rates and physiologic thresholds for metabolic and hemodynamic actions in man" J Clin Invest. (1980) 66(1):94-101.

Czupryniak et al., "Ambulatory Glucose Profile (AGP) Report in Daily Care of Patients with Diabetes: Practical Tips and Recommendations" Diabetes Ther (2022) 13:811-821.

Donnelly et al., "Microneedle Arrays Allow Lower Microbial Penetration Than Hypodermic Needles In Vitro" Pharmaceutical Research (2009) 26(11):2513-2522.

Fayfman et al., "Management of Hyperglycemic Crises: Diabetic ketoacidosis and hyperglycemic hyperosmolar state" Med Clin North Am. (2017) May; 101(3):587-606.

Ghimire et al., "Ketoacidosis" StatPearls Publishing, Jan. 2024, NCBI Bookshelf, 8 pages.

Heinemann, "Interferences With CGM Systems: Practical Relevance?" Journal of Diabetes Science and Technology (2022) vol. 16(2) 271-274.

Henry et al., "Microfabricated microneedles: A novel approach to transdermal drug delivery" J. Pharmaceutical Sciences (1998) 87(8):922-925.

Jina, A et al. (2014). "Design, development, and evaluation of a novel microneedle array-based continuous glucose monitor," J. Diabetes Sci. Technol. 8:483-487.

Mahs et al., "Effect of Acetaminophen on CGM Glucose in an Outpatient Setting" Diabetes Care (2015) 38:e158-e159.

Nguyen et al., "Human studies with microneedles for evaluation of their efficacy and safety" Expert Opinion on Drug Delivery (2018) 15:3, 235-245.

Non-Final Office Action for U.S. Appl. No. 17/389,156 mailed Jan. 22, 2025, 17 pages.

Ohashi et al., "Analgesic Effect of Acetaminophen: A Review of Known and Novel Mechanisms of Action" Front Pharmacol. (2020) Nov. 30;11:580289, 6 pages.

Prausnitz, "Engineering Microneedle Patches for Vaccination and Drug Delivery to Skin" Annu. Rev. Chem. Biomol. Eng. (2017) 8:177-200.

Samant et al., "Mechanisms of sampling interstitial fluid from skin using a microneedle patch," Proc. Natl Acad. Sci. U.S.A. (2018) 115(8):4583-4588.

Vicente-Perez et al., "Repeat application of microneedles does not alter skin appearance or barrier function and causes no measurable disturbance of serum biomarkers of infection, inflammation or immunity in mice in vivo" European Journal of Pharmaceutics and Biopharmaceutics (2017) 117:400-407.

Yue et al., "Evaluation of a 12-Hour Sustained-Release Acetaminophen (Paracetamol) Formulation: A Randomized, 3-Way Crossover Pharmacokinetic and Safety Study in Healthy Volunteers" Clinical Pharmacology in Drug Development (2018) 7(1) 95-101.

* cited by examiner

100

120

110

130

135

200

120

110

130

135

SOLID-STATE SUBSTRATE-INTEGRATED REFERENCE ELECTRODE AND COUNTER ELECTRODE

CROSS REFERENCE TO RELATED APPLICATIONS

This application claims priority to U.S. Provisional Patent Application No. 63/121,223, filed Dec. 3, 2020, and entitled "Solid-State Substrate-Integrated Reference Electrodes Providing for Functional Layer Electrodeposition and Methods for the Realization of Same," the content of which is herein incorporated by reference in its entirety.

BACKGROUND

Electrochemical deposition involves a method of deposition of a sensing layer on a sensing element. To achieve the electrochemical deposition of the sensing layer, a stable reference is required. The stable reference may take the form of a reference electrode that provides a stable electrode voltage to facilitate the electrochemical deposition within an electrolytic cell.

SUMMARY

Aspects of the current subject matter are directed to a reference electrode integrated on a surface of a substrate to facilitate functionalization of a working electrode. Additional aspects of the current subject matter are directed to a counter electrode integrated on a surface of a substrate.

Aspects of the current subject matter are directed to a device comprising a substrate, a reference electrode, and a working electrode, wherein the reference electrode and the working electrode form an electrolytic cell in a fluid medium, and wherein application of an electrical stimulus to the working electrode in the electrolytic cell provides electrodeposition of a surface layer on the working electrode. In some embodiments, the working electrode is positioned on an anterior surface of the substrate. In some embodiments, the reference electrode comprises a transducer positioned on the anterior surface of the substrate, and an overlay comprising a redox couple applied to a first surface of the transducer. In some embodiments, the redox couple comprises Ag/AgCl, Cu/CuSO$_4$, or Ir$_2$O$_3$/IrO$_2$. In some embodiments, said redox couple facilitates the formation of a stable electrode potential, optionally between −1.5 volts and +1.5 volts versus a standard hydrogen electrode. In some embodiments, the device is an analyte-selective sensor, and the working electrode comprises a sensing element.

In some embodiments, the surface layer of the working electrode comprises at least one selected from the group of a sensing layer, a biorecognition layer, a diffusion limiting layer, a biocompatible layer, and an interference rejection layer. In some embodiments, the working electrode comprises at least one selected from the group of a metal, a metal alloy, a semiconductor, and a polymer. In some embodiments, the substrate comprises at least one selected from the group of a printed circuit board, a flexible circuit, a polymer, and a semiconductor device. In some embodiments, the transducer comprises at least one selected from the group of a trace, an electrode, a pad, a via, a contact point, and an electrical connector. In some embodiments, the transducer comprises at least one selected from the group of a metal, a metal alloy, and a metal oxide. In some embodiments, the overlayer comprises at least one selected from the group of a metal, a metal alloy, a metal oxide, a metal salt, a metal dispersion, a metal ink, a metal paste, a semiconductor, and a conducting polymer.

In some embodiments, the application of the electrical stimulus comprises one or more selected from the group of amperometry, chronoamperometry, coulometry, voltammetry, cyclic voltammetry, linear sweep voltammetry, a galvanic electrochemical application, and a potentiometric electrochemical application. In some embodiments, the electrolytic cell comprises a counter electrode. In some embodiments, the fluid medium comprises at least one selected from the group of an aqueous solution, an electrolytic solution, an ionic liquid, a solvent, or a dispersion.

Aspects of the current subject matter are directed to a method comprising providing a device comprising a substrate, a reference electrode, and a working electrode, wherein the reference electrode and the working electrode are positioned on an anterior surface of the substrate and form an electrolytic cell in a fluid medium, and wherein the reference electrode comprises a transducer positioned on the anterior surface of the substrate and an overlay comprising a redox couple applied to a first surface of the transducer, immersing the device in a fluid medium, and applying an electrical stimulus to the working electrode, thereby causing electrodeposition of a surface layer on the working electrode. In some embodiments, the redox couple comprises Ag/AgCl, Cu/CuSO$_4$, or Ir$_2$O$_3$/IrO$_2$. In some embodiments, said redox couple facilitates the formation of a stable electrode potential. In some embodiments, the stable electrode potential is between −1.5 volts and +1.5 volts versus a standard hydrogen electrode. In some embodiments, the working electrode is a sensing element in an analyte-selective sensor.

In some embodiments, the surface layer comprises at least one selected from the group of a sensing layer, a biorecognition layer, a diffusion limiting layer, a biocompatible layer, and an interference rejection layer. In some embodiments, the working electrode comprises at least one selected from the group of a metal, a metal alloy, a semiconductor, and a polymer. In some embodiments, the substrate comprises at least one selected from the group of a printed circuit board, a flexible circuit, a polymer, and a semiconductor device. In some embodiments, the transducer comprises at least one selected from the group of a trace, an electrode, a pad, a via, a contact point, and an electrical connector. In some embodiments, the transducer comprises at least one selected from the group of a metal, a metal alloy, and a metal oxide. In some embodiments, the overlayer comprises at least one selected from the group of a metal, a metal alloy, a metal oxide, a metal salt, a metal dispersion, a metal ink, a metal paste, a semiconductor, and a conducting polymer.

In some embodiments, the application of the electrical stimulus comprises one or more selected from the group of amperometry, chronoamperometry, coulometry, voltammetry, cyclic voltammetry, linear sweep voltammetry, a galvanic electrochemical application, and a potentiometric electrochemical application. In some embodiments, the electrolytic cell comprises a counter electrode. In some embodiments, the fluid medium comprises at least one selected from the group of an aqueous solution, an electrolytic solution, an ionic liquid, a solvent, and a dispersion.

Both the foregoing general description and the following detailed description are exemplary and explanatory only and are not restrictive. Further features and/or variations may be provided in addition to those set forth herein. For example, the implementations described herein may be directed to various combinations and sub-combinations of the disclosed features.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
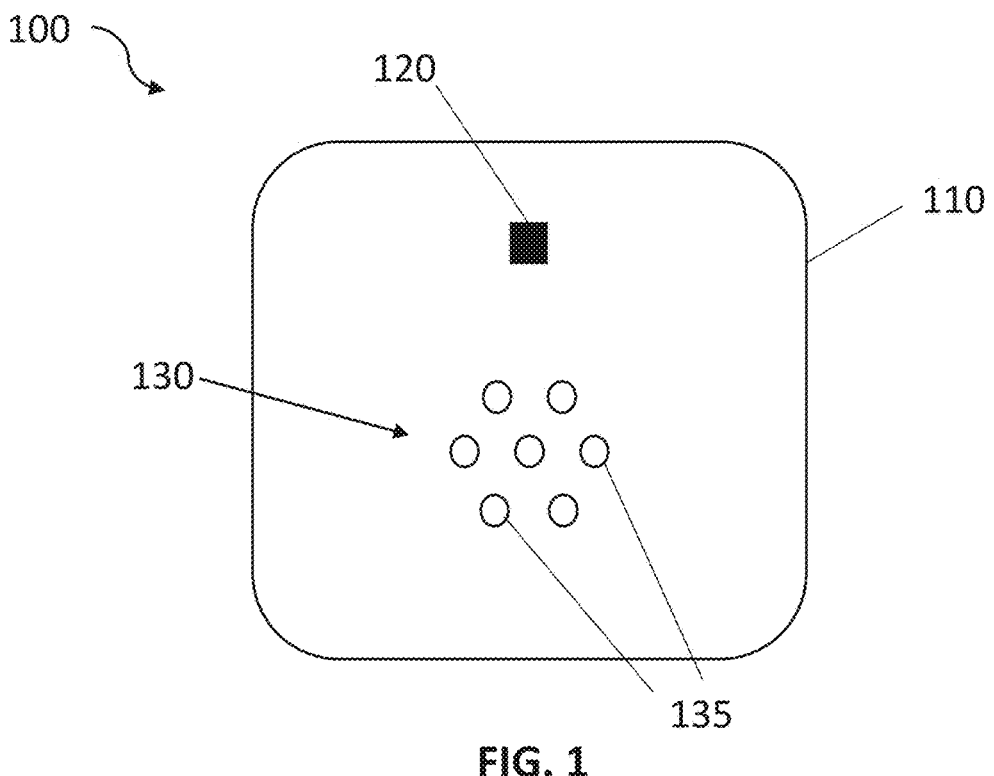
FIG. 1 depicts an illustrative schematic of a substrate with an integrated reference electrode in accordance with implementations of the current subject matter.

Aspects of the current subject matter are directed to a reference electrode integrated on a surface of a substrate to facilitate functionalization of a working electrode. The reference electrode, according to implementations of the current subject matter, is used in electrochemical deposition (also referred to as electrodeposition) of one or more functional layers on a working electrode. The working electrode may be, for example, a sensing element of an analyte-selective sensor. Additional aspects of the current subject matter are directed to a counter electrode integrated on a surface of a substrate.

In an implementation of an analyte-selective sensor, deposition of one or more analyte-selective layers on the working electrode functioning as a sensing element is required. Electrodeposition is a method that provides uniformity of the analyte-selective layers and that allows for the control of the quantity of deposit to a high degree of precision. To achieve the electrodeposition of the one or more sensing layers, a stable reference is required. The stable reference may take the form of a reference electrode.

In conventional systems or applications, the reference electrode may be, for example, a metal wire immersed in an internal filling solution and containing a liquid junction. Although this implementation may be achievable in scientific and laboratory settings, difficulties exist in scaling the use of liquid-junction reference electrodes to industrial processes where there is a high degree of parallelization. In such applications, a reference electrode architecture that removes the need for an external device to impart a stable electrode voltage required for electrolytic reactions would enable the highly parallelized synthesis of analyte-selective sensors in commercial settings.

Accordingly, aspects of the current subject matter provide a solid-state reference electrode integrated on the surface of a substrate in fluid contact with an electrolytic cell for the purpose of facilitating the electrochemical synthesis of one or more functional layers on a working electrode located within the electrolytic cell.

Electrochemical deposition is a technique used to deposit films of conducting chemical species dissolved within a bulk solution. In this process, a chemical species undergoes a reduction or oxidation reaction and thereby deposits as a film at a cathode or anode, respectively, in an electrolytic process at a certain bias potential. To drive the redox reaction at a defined and controllable rate, the electrical potential at either the anode or cathode must be established at a particular value, which will instigate the flow of an electrical current between the two electrodes. To prevent the likelihood of a large ohmic drop due to current flow in an electrolytic solution of finite resistance, which could cause the potential to deviate from the intended value, a third electrode—a reference electrode—from which a stable potential is referenced with respect to the anode or cathode is provided. The function of the reference electrode is to provide a thermodynamically stable electrode potential, which is not subject to perceptible change in characteristic performance over varying test conditions, from which an electrolytic reaction is referenced. The reference electrode is not involved in the electron transfer reaction occurring between the anode and cathode (e.g., operates at zero current) and itself employs a reversible redox couple to establish a stable and well-characterized electrode potential. This requires the implementation of a semi-sealed system containing the redox couple, immersed or dispersed within a liquid-phase solution or an aqueous-phase solution, with a means to facilitate ohmic contact with the bulk solution. The reference electrode establishes a half-cell constituent required to build a stable electrochemical cell.

Aspects of the current subject matter provide a solid-state reference electrode integrated directly onto a substrate, thereby forming an integrated reference electrode. The integrated reference electrode enables the electrodeposition process of functional layers on one or more working electrodes. In some variations, the integrated reference electrode is intended for use only during the electrodeposition process.

In some variations, the implementation of a solid-state, substrate-integrated reference electrode enables the electrodeposition of functional layers (e.g., surface-immobilized layers) on at least one working electrode located within an analyte-selective sensor to be applied to an anatomy (e.g., on a human body). The solid-state, substrate-integrated reference electrode enables the synthesis of analyte-selective sensors in a highly parallelized fashion that obviates the need for delicate and cumbersome liquid-junction reference electrodes.

In some variations, the integrated reference electrode is located on a surface of a printed circuit board. In some variations, the integrated reference electrode is located on a surface of a flexible circuit board. In some variations, the integrated reference electrode is located on a surface of a semiconductor device, for example, an integrated circuit or a microelectromechanical system (MEMS).

The integrated reference electrode includes, in some variations, a transducer layer located on an anterior surface of a substrate and a redox-active overlayer. The redox-active overlayer includes a redox couple having a known and stable electrode potential.

The reference electrode, by merit of immersion in the same solution as the working electrode and optionally a counter electrode, completes an electrolytic cell, along with the working electrode and the optional counter electrode. The integrated reference electrode provides for simplified parallelization of batch electrolysis or electrodeposition processes, eases scale up to high volume manufacture, and reduces cost of bulky components and their maintenance.

In some variations, a reference electrode device includes a substrate, a transducer, and an overlayer containing a redox couple applied to an anterior surface of the transducer. The reference electrode is used as a component of an electrolytic cell and configured to operate in the same fluid medium as a working electrode.

Figure 2:
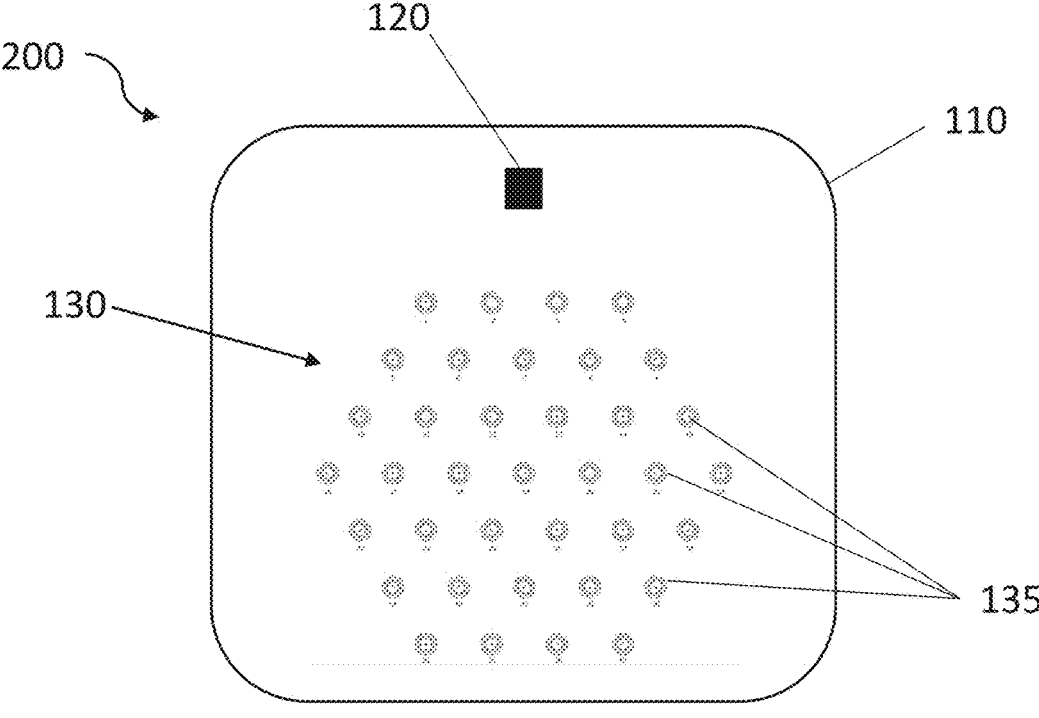
FIG. 2 depicts an illustrative schematic of a substrate with an integrated reference electrode in accordance with implementations of the current subject matter.

FIG. 1 depicts an illustrative schematic of a device 100 including a substrate 110 with an integrated reference electrode 120 in accordance with implementations of the current subject matter. The device 100 also includes a plurality of electrodes 130, including one or more working electrodes 135. The integrated reference electrode 120 and the plurality of electrodes 130 are positioned on an anterior surface of the substrate 110. FIG. 2 depicts an illustrative schematic of a device 200, similar to the device 100 of FIG. 1. An integrated reference electrode 120 and a plurality of electrodes 130, including one or more working electrodes 135, are positioned on an anterior surface of the substrate 110.

Figure 6A:
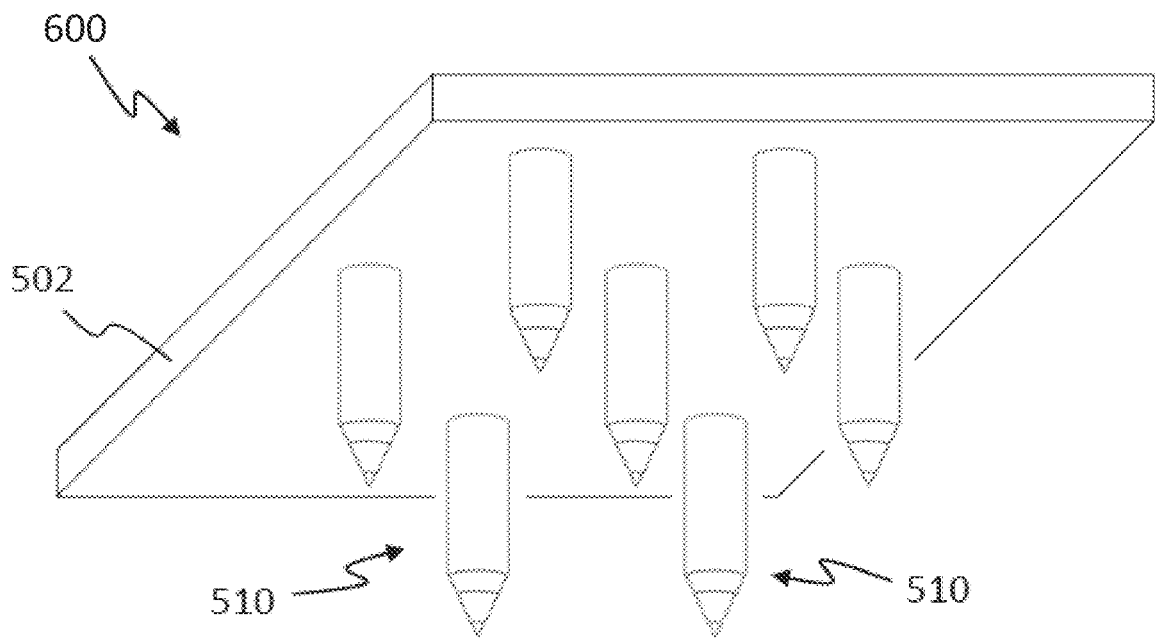
FIG. 6A depicts an illustrative schematic of a microneedle array.
Figure 6B:
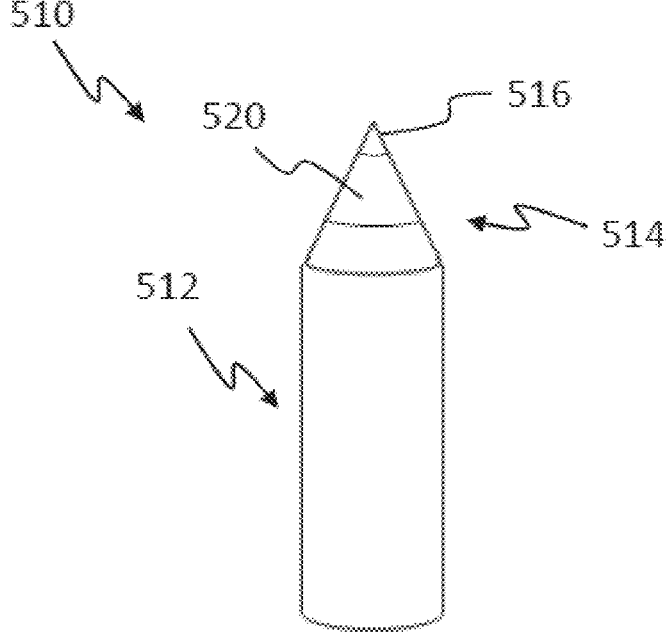
FIG. 6B depicts an illustrative schematic of a microneedle in the microneedle array depicted in FIG. 6A.

Reference is made to device 100 shown in FIG. 1 and device 200 shown in FIG. 2. The number of the plurality of electrodes 130 is not limited to a particular value, and any number of electrodes 130 may be incorporated. The device 100 includes seven electrodes 130, and the device 200 includes 37 electrodes 130. In other variations, any number of electrodes may be incorporated. Moreover, the configuration of the plurality of electrodes 130 is not limited to a particular arrangement, and the plurality of electrodes 130 may be arranged in various types of configurations. Substrate 110 may, for example, have a surface that is generally planar. In some variations, working electrodes 135 may be shaped as or be comprised in microneedles projecting from the surface of substrate 110. In some variations, a microneedle comprising working electrode 135 may be configured as shown in FIGS. 6A and 6B and described hereinbelow with respect to microneedles 510. In some variations, working electrode 135 may be located on a surface of a tapered distal portion of the microneedle, as shown with respect to electrode 520 in FIGS. 6A and 6B. In some variations, reference electrode 120 may have a planar surface that is substantially parallel with the surface of substrate 110. In some variations, the surface of reference electrode 120 may be flush with or be indented with respect to the surface of substrate 110.

Figure 3:
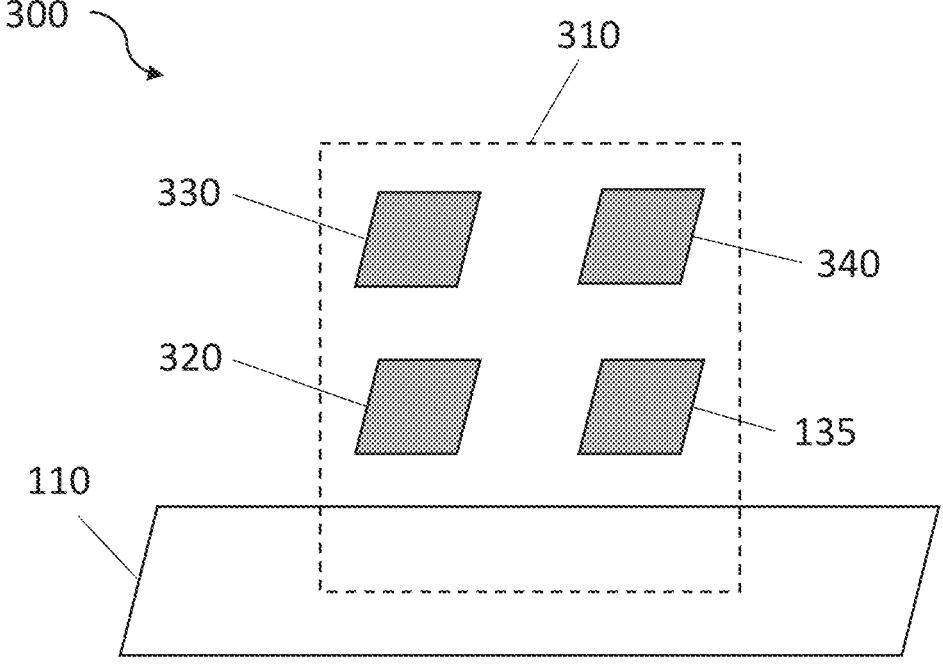
FIG. 3 depicts an illustrative schematic of a substrate with an electrolytic cell in accordance with implementations of the current subject matter.

FIG. 3 depicts an illustrative schematic of a device 300 with a substrate 110 and an electrolytic cell 310 in accordance with implementations of the current subject matter. A reference electrode 120 is formed from a transducer 320 with an overlay 330. In some variations, the overlay 330 includes a redox couple applied to a first (e.g., top) surface of the transducer 320. A working electrode 135, along with the reference electrode 120 in a fluid medium (not shown) form the electrolytic cell 310. In accordance with aspects of the current subject matter, application of an electrical stimulus to the working electrode 135 results in electrodeposition of a surface layer 340 on an exposed surface of the working electrode 135. In some variations, the surface layer 340, also referred to as a surface-immobilized layer, is one or more of a functional layer, a membrane, a film, a sensing layer, a biorecognition layer, a diffusion limiting layer, a biocompatible layer, and an interference rejection layer.

As shown in FIG. 3, the electrolytic cell 310 positioned on the substrate 110 includes the transducer 320, the working electrode 135, and the overlay 330 with an embedded redox couple and the surface layer 340.

Figure 4:
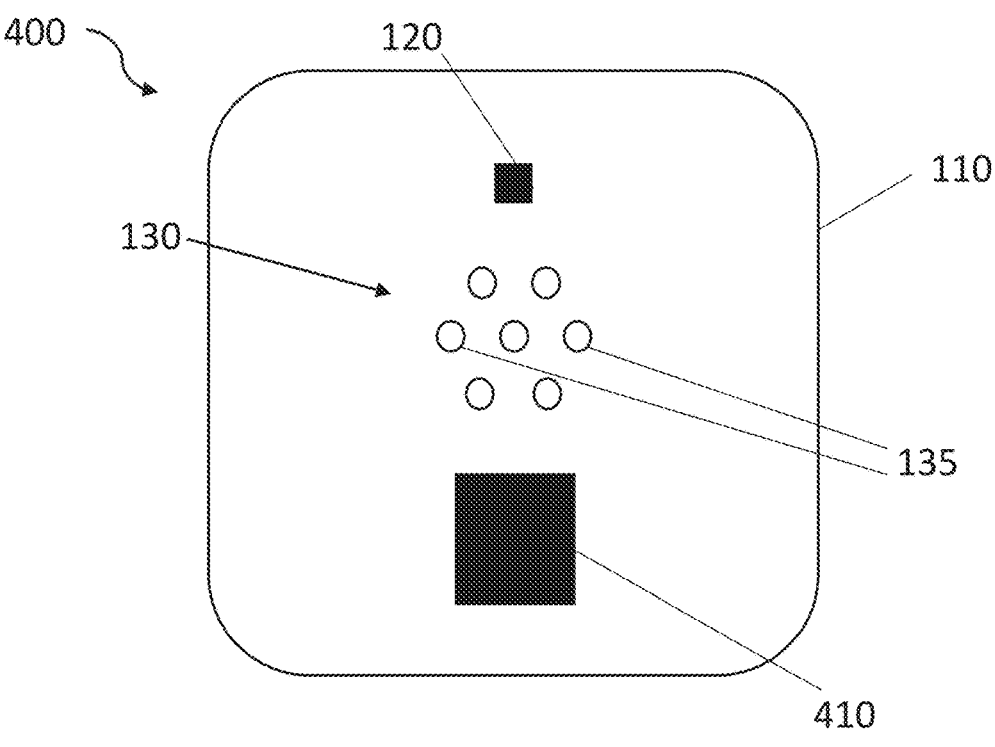
FIG. 4 depicts an illustrative schematic of a substrate with an integrated reference electrode and an integrated counter electrode in accordance with implementations of the current subject matter.
Figure 5:
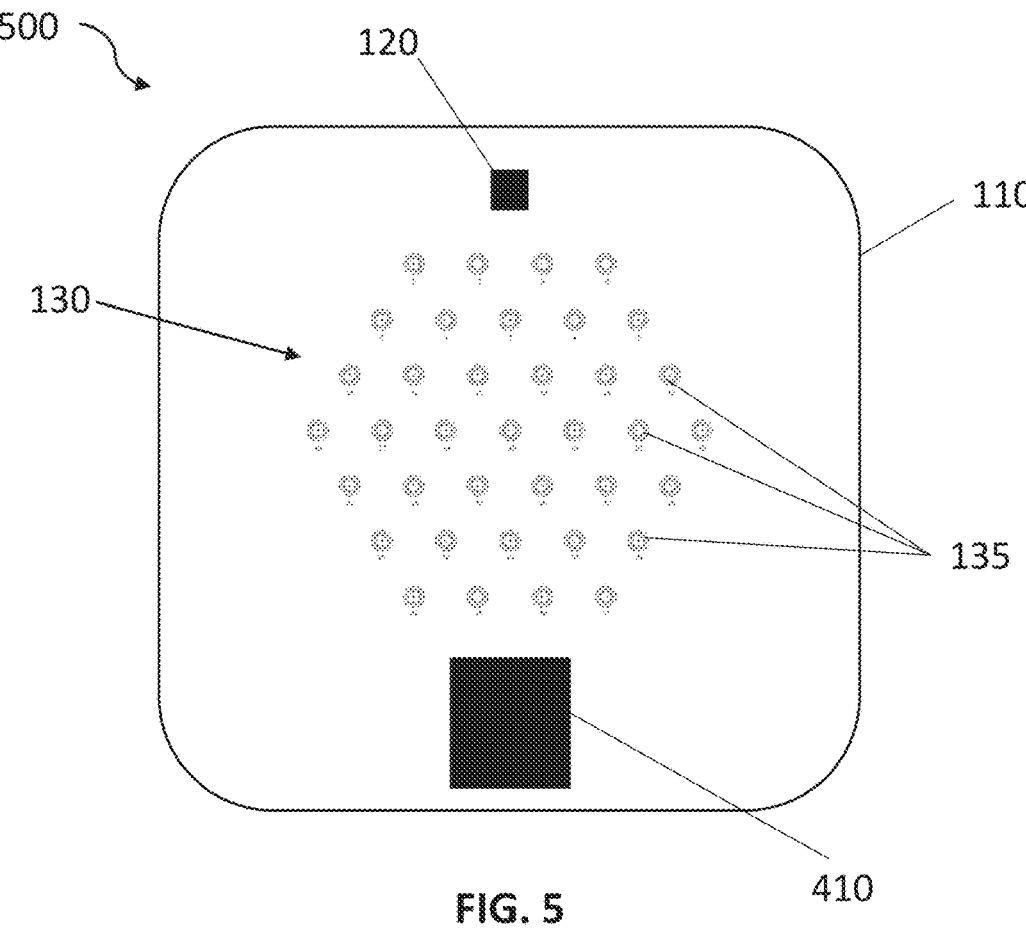
FIG. 5 depicts an illustrative schematic of a substrate with an integrated reference electrode and an integrated counter electrode in accordance with implementations of the current subject matter.

FIG. 4 and FIG. 5 depict a device 400 and a device 500, respectively, having an integrated reference electrode 120 and a plurality of electrodes 130, including one or more working electrodes 135. The device 400 and the device 500 further include a counter electrode 410, also referred to as an auxiliary electrode. The number of the plurality of electrodes 130 is not limited to a particular value, and any number of electrodes 130 may be incorporated. The device 100 includes seven electrodes 130, and the device 200 includes 37 electrodes 130. In other variations, any number of electrodes may be incorporated. Moreover, the configuration of the plurality of electrodes 130 is not limited to a particular arrangement, and the plurality of electrodes 130 may be arranged in various types of configurations. Substrate 110 may, for example, have a surface that is generally planar. In some variations, working electrodes 135 may be shaped as or be comprised in microneedles projecting from the surface of substrate 110. In some variations, a microneedle comprising working electrode 135 may be configured as shown in FIGS. 6A and 6B and described hereinbelow with respect microneedles 510. In some variations, working electrode 135 may be located on a surface of a tapered distal portion of the microneedle, as shown with respect to electrode 520 in FIGS. 6A and 6B. In some variations, reference electrode 120 and/or counter electrode 410 may have a planar surface that is substantially parallel with the surface of substrate 110. In some variations, the surface of reference electrode 120 and/or counter electrode 410 may be flush with or be indented with respect to the surface of substrate 110.

The counter electrode 410 functions to source (provide) or sink (accumulate) electrons, via an electrical current, that are required to sustain the electrochemical reaction at the working electrode. To handle the electrical current, the counter electrode 410 must be of a sufficient size. In some variations, the counter electrode 410 is about ten times the size of a working electrode. In some variations, the counter electrode 410 is between five and 15 times the size of a working electrode. In some variations, the counter electrode 410 is about five, about six, about seven, about eight, about nine, about 10, about eleven, about twelve, about thirteen, about fourteen, or about fifteen times the size of a working electrode. In certain variations, the size of the counter electrode compared to the working electrode refers to a surface area of the respective electrodes.

FIG. 6A depicts a microneedle array 600 in which the current subject matter may be implemented. The microneedle array 600 for use in sensing one or more analytes may include one or more microneedles 510 projecting from a substrate surface 502. The substrate surface 502 may, for example, be generally planar. The one or more microneedles 510 may project orthogonally from the planar surface. Generally, as shown in FIG. 6B, a microneedle 510 may include a body portion 512 (e.g., shaft) and a tapered distal portion 514 configured to puncture skin of a user. In some variations, the tapered distal portion 514 may terminate in an insulated distal apex 516. The microneedle 510 may further include an electrode 520 on a surface of the tapered distal portion. In some variations, electrode-based measurements may be performed at the interface of the electrode and interstitial fluid located within the body (e.g., on an outer surface of the overall microneedle). In some variations, the microneedle 510 may have a solid core (e.g., solid body portion), though in some variations the microneedle 510 may include one or more lumens, which may be used for drug delivery or sampling of the dermal interstitial fluid, for example. Other microneedle variations may similarly either include a solid core or one or more lumens.

The microneedle array 600 may be at least partially formed from a semiconductor (e.g., silicon) substrate and include various material layers applied and shaped using various suitable microelectromechanical systems (MEMS) manufacturing techniques (e.g., deposition and etching techniques), as further described below. The microneedle array may be reflow-soldered to a circuit board, similar to a typical integrated circuit. Furthermore, in some variations the microneedle array 600 may include a three-electrode setup including a working (sensing) electrode having an electrochemical sensing coating (including a biorecognition element such as an enzyme) that enables detection of a target analyte, a reference electrode, and a counter electrode. In other words, the microneedle array 600 may include at least one microneedle 510 that includes a working electrode, at least one microneedle 510 including a reference electrode, and at least one microneedle 510 including a counter electrode. Additional details of these types of electrodes are described in further detail below.

In some variations, the microneedle array 600 may include a plurality of microneedles that are insulated such that the electrode on each microneedle in the plurality of microneedles is individually addressable and electrically isolated from every other electrode on the microneedle array. The resulting individual addressability of the microneedle array 600 may enable greater control over each electrode's function since each electrode may be separately probed. For example, the microneedle array 600 may be used to provide multiple independent measurements of a given target analyte, which improves the device's sensing reliability and accuracy. Furthermore, in some variations the electrodes of multiple microneedles may be electrically connected to produce augmented signal levels. As another example, the same microneedle array 600 may additionally or alternatively be interrogated to simultaneously measure multiple analytes to provide a more comprehensive assessment of physiological status. For example, a microneedle array may include a portion of microneedles to detect a first Analyte A, a second portion of microneedles to detect a second Analyte B, and a third portion of microneedles to detect a third Analyte C. The microneedle array may be configured to detect any suitable number of analytes (e.g., 1, 2, 3, 4, 5 or more, etc.). Suitable target analytes for detection may, for example, include glucose, ketones, lactate, and cortisol. Thus, individual electrical addressability of the microneedle array 600 provides greater control and flexibility over the sensing function of the analyte monitoring device.

In some variations of microneedles (e.g., microneedles with a working electrode), the electrode 520 may be located proximal to the insulated distal apex 516 of the microneedle. In other words, in some variations the electrode 520 does not cover the apex of the microneedle. Rather, the electrode 520 may be offset from the apex or tip of the microneedle. The electrode 520 being proximal to or offset from the insulated distal apex 516 of the microneedle advantageously provides more accurate sensor measurements. For example, this arrangement prevents concentration of the electric field at the microneedle apex 516 during manufacturing, thereby avoiding non-uniform electro-deposition of sensing chemistry on the electrode surface 520 that would result in faulty sensing.

As another example, placing the electrode 520 offset from the microneedle apex further improves sensing accuracy by reducing undesirable signal artefacts and/or erroneous sensor readings caused by stress upon microneedle insertion. The distal apex of the microneedle is the first region to penetrate the skin, and thus experiences the most stress caused by the mechanical shear phenomena accompanying the tearing or cutting of the skin. If the electrode 520 were placed on the apex or tip of the microneedle, this mechanical stress may delaminate the electrochemical sensing coating on the electrode surface when the microneedle is inserted, and/or cause a small yet interfering amount of tissue to be transported onto the active sensing portion of the electrode. Thus, placing the electrode 520 sufficiently offset from the microneedle apex may improve sensing accuracy. For example, in some variations, a distal edge of the electrode 520 may be located at least about 10 µm (e.g., between about 20 µm and about 30 µm) from the distal apex or tip of the microneedle, as measured along a longitudinal axis of the microneedle.

The body portion 512 of the microneedle 510 may further include an electrically conductive pathway extending between the electrode 520 and a backside electrode or other electrical contact (e.g., arranged on a backside of the substrate of the microneedle array). The backside electrode may be soldered to a circuit board, enabling electrical communication with the electrode 520 via the conductive pathway. For example, during use, the in-vivo sensing current (inside the dermis) measured at a working electrode is interrogated by the backside electrical contact, and the electrical connection between the backside electrical contact and the working electrode is facilitated by the conductive pathway. In some variations, this conductive pathway may be facilitated by a metal via running through the interior of the microneedle body portion (e.g., shaft) between the microneedle's proximal and distal ends. Alternatively, in some variations the conductive pathway may be provided by the entire body portion being formed of a conductive material (e.g., doped silicon). In some of these variations, the complete substrate on which the microneedle array 600 is built upon may be electrically conductive, and each microneedle 510 in the microneedle array 600 may be electrically isolated from adjacent microneedles 510 as described below. For example, in some variations, each microneedle 510 in the microneedle array 600 may be electrically isolated from adjacent microneedles 510 with an insulative barrier including electrically insulative material (e.g., dielectric material such as silicon dioxide) that surrounds the conductive pathway extending between the electrode 520 and backside electrical contact. For example, body portion 512 may include an insulative material that forms a sheath around the conductive pathway, thereby preventing electrical communication between the conductive pathway and the substrate. Other example variations of structures enabling electrical isolation among microneedles are described in further detail below.

Such electrical isolation among microneedles in the microneedle array permits the sensors to be individually addressable. This individually addressability advantageously enables independent and parallelized measurement among the sensors, as well as dynamic reconfiguration of sensor assignment (e.g., to different analytes). In some variations, the electrodes in the microneedle array can be configured to provide redundant analyte measurements, which is an advantage over conventional analyte monitoring devices. For example, redundancy can improve performance by improving accuracy (e.g., averaging multiple analyte measurement values for the same analyte which reduces the effect of extreme high or low sensor signals on the determination of analyte levels) and/or improving reliability of the device by reducing the likelihood of total failure.

In some variations, the microneedle array may be formed at least in part with suitable semiconductor and/or MEMS fabrication techniques and/or mechanical cutting or dicing. Such processes may, for example, be advantageous for enabling large-scale, cost-efficient manufacturing of microneedle arrays.

As described above, each microneedle in the microneedle array may include an electrode. In some variations, multiple distinct types of electrodes may be included among the microneedles in the microneedle array. For example, in some variations the microneedle array may function as an electrochemical cell operable in an electrolytic manner with three types of electrodes. In other words, the microneedle array may include at least one working electrode, at least one counter electrode, and at least one reference electrode. Thus, the microneedle array may include three distinct electrode types, though one or more of each electrode type may form a complete system (e.g., the system might include multiple distinct working electrodes). Furthermore, multiple distinct microneedles may be electrically joined to form an effective electrode type (e.g., a single working electrode may be formed from two or more connected microneedles with working electrode sites). Each of these electrode types may include a metallization layer and may include one or more coatings or layers over the metallization layer that help facilitate the function of that electrode.

Generally, the working electrode is the electrode at which oxidation and/or reduction reaction of interest occurs for detection of an analyte of interest. The counter electrode functions to source (provide) or sink (accumulate) the electrons, via an electrical current, that are required to sustain the electrochemical reaction at the working electrode. The reference electrode functions to provide a reference potential for the system; that is, the electrical potential at which the working electrode is biased is referenced to the reference electrode. A fixed, time-varying, or at least controlled potential relationship is established between the working and reference electrodes, and within practical limits no current is sourced from or sinked to the reference electrode. Additionally, to implement such a three-electrode system, the analyte monitoring device may include a suitable potentiostat or electrochemical analog front end to maintain a fixed potential relationship between the working electrode and reference electrode contingents within the electrochemical system (via an electronic feedback mechanism), while permitting the counter electrode to dynamically swing to potentials required to sustain the redox reaction of interest.

According to an implementation of the current subject matter, a method is provided for the electrodeposition of at least one surface-immobilized layer on at least one working electrode contained within a body-worn analyte-selective sensor. The method includes applying an overlayer containing a redox couple on the anterior surface of a transducer located on a surface of a substrate, thereby forming a substrate-integrated reference electrode. The substrate-integrated reference electrode is immersed in a fluid medium containing the least one working electrode, thereby forming an electrolytic cell. An electrical stimulus is applied to the least one working electrode. The application of the electrical stimulus effects the electrodeposition of the surface-immobilized layer on the at least one working electrode contained within a body-worn analyte-selective sensor.

Various layers of the working electrode, counter electrode, and reference electrode may be applied to the microneedle array and/or functionalized, etc. using suitable processes such as those described below.

In a pre-processing step for the microneedle array, the microneedle array may be plasma cleaned in an inert gas (e.g., RF-generated inert gas such as argon) plasma environment to render the surface of the material, including the electrode material, to be more hydrophilic and chemically reactive. This pre-processing functions to not only physically remove organic debris and contaminants, but also to clean and prepare the electrode surface to enhance adhesion of subsequently deposited films on its surface.

Anodization: To configure the working electrode after the pre-processing step, the electrode material may undergo an anodization treatment using an amperometry approach in which the electrode constituent(s) assigned for the working electrode function is (are) subject to a fixed high anodic potential (e.g., between +1.0 and +1.3 V vs. Ag/AgCl reference electrode) for a suitable amount of time (e.g., between about 30 sec and about 10 min) in a moderate-strength acid solution (e.g., 0.1-3M $H_2SO_4$). In this process, a thin, yet stable native oxide layer may be generated on the electrode surface. Owing to the low pH arising at the electrode surface, any trace contaminants may be removed as well.

In an alternative embodiment using a coulometry approach, anodization can proceed until a specified amount of charge has passed (measured in Coulombs). The anodic potential may be applied as described above; however, the duration of this might vary until the specified amount of charge has passed.

Activation: Following the anodization process, the working electrode constituents may be subjected to a cyclically scanned potential waveform in an activation process using cyclic voltammetry. In the activation process, which may occur in a moderate-strength acid solution (e.g. between 0.1M and 3M $H_2SO_4$), the potential applied may time-varying in a suitable function (e.g., sawtooth function). For example, the voltage may be linearly scanned between a cathodic value (e.g., between −0.3 and −0.2 V vs. Ag/AgCl reference electrode) and an anodic value (e.g., between +1.0 and +1.3 V vs. Ag/AgCl reference electrode) in an alternating function (e.g., between 15 and 50 linear sweep segments). The scan rate of this waveform can take on a value between 1 and 1000 mV/sec. It should be noted that a current peak arising during the anodic sweep (sweep to positive extreme) corresponds to the oxidation of a chemical species, while the current peak arising during the ensuing cathodic sweep (sweep to negative extreme) corresponds to the reduction of said chemical species.

Functionalization of the biorecognition layer: Following the activation process, the working electrode constituents may be functionalized with the biorecognition layer such as that described above. Assuming that the working electrode contingent of the microneedle array has undergone the aforementioned steps, the potential applied may be time-varying in a sawtooth function. For example, a voltage may be linearly scanned between a cathodic value (e.g., about 0.0 V vs. Ag/AgCl reference electrode) and an anodic value (e.g., about +1.0 V vs Ag/AgCl reference electrode) in an alternating function (e.g., 10 linear sweep segments). In an example variation, the scan rate of this waveform can take on a value between about 1 mV/sec and about 10 mV/sec in an aqueous solution comprised of a monomeric precursor to the entrapment conducting polymer and a cross-linked biorecognition element (e.g., enzyme, such as glucose oxidase). In this process, a thin film (e.g., between about 10 nm and about 1000 nm) of biorecognition layer comprising of polymer with a dispersed cross-linked biorecognition element may be generated (e.g., electrodeposited or electropolymerized) on the working electrode surface. In some variations, the conducting polymer may include one or more of aniline, pyrrole, acetylene, phenylene, phenylene vinylene, phenylene diamine, thiophene, 3,4-ethylenedioxythiophene, and aminophenylboronic acid. The biorecognition layer imparts a selective sensing capability towards an analyte of interest, as described above.

In some variations, the working electrode surface may be electrochemically roughened in order to enhance adhesion of the biorecognition layer to the electrode material surface (and/or Pt black layer). The roughening process may involve a cathodization treatment (e.g., cathodic deposition, a subset of amperometry) wherein the electrode is subject to a fixed cathodic potential (e.g., between −0.4 and +0.2 V vs. Ag/AgCl reference electrode) for a certain amount of time (e.g., between 5 sec and 10 min) in an acid solution containing the desired metal cation dissolved therein (e.g., between 0.01 and 100 mM $H_2PtCl_6$). Alternatively, the electrode is subject to a fixed cathodic potential (e.g., between about −0.4 and about +0.2 V vs. Ag/AgCl reference electrode) until a certain amount of charge has passed (e.g., between 0.1 mC and 100 mC) in an acid solution containing the desired metal cation dissolved therein (e.g., between 0.01 and 100 mM $H_2PtCl_6$). In this process, a thin, yet highly porous layer of the metal may be generated on the electrode surface, thereby augmenting the electrode surface area dramatically. Additionally or alternatively, in some variations as described above, elemental platinum metal may be deposited on the electrode to form or deposit a platinum black layer 1613.

Functionalization of the diffusion-limiting layer: Following the functionalization of the biorecognition layer, the working electrode constituents may, in some variations, be functionalized with the diffusion-limiting layer. Assuming that the working electrode contingent of the microneedle array has undergone the aforementioned steps, one or more of the following methods may be employed to apply the diffusion-limiting layer, which may be a thin film of thickness between about 100 nm to about 10,000 nm.

In some variations, a diffusion-limiting layer may be applied by a spray coating method in which an aerosolized polymer formulation (dispersed in water or a solvent) is applied to the microneedle array device with a specified spray pattern and duration in a controlled-environment setting. This creates a thin film with the desired thickness and porosity required to restrict the diffusion of an analyte of interest to the biorecognition layer.

In some variations, a diffusion-limiting layer may be applied by a plasma-induced polymerization method in which a plasma source generates a gas discharge that provides energy to activate a cross-linking reaction within a gaseous, aerosolized, or liquid monomeric precursor (e.g., vinylpyridine). This converts the monomeric precursor to a polymeric coating that may be deposited on the microneedle array to a specified thickness, thereby creating a thin film with the desired thickness and porosity required to restrict the diffusion of an analyte of interest to the biorecognition layer.

Furthermore, in some variations, a diffusion-limiting layer may be applied by electrophoretic or dielectrophoretic deposition.

Anodization: In some variations, the counter electrode material may undergo an anodization treatment using an amperometry approach in which the electrode constituent(s) assigned for the counter electrode function is subject to a fixed high anodic potential or a suitable amount of time in a moderate-strength acid solution. Exemplary parameters and other specifics of the anodization process for the counter electrode may be similar to that described above for the working electrode. Similarly, anodization for the counter electrode may alternatively use a coulometry approach as described above.

Activation: In some variations, following the anodization process, the counter electrode constituents may be subjected to a cyclically scanned potential waveform in an activation process using cyclic voltammetry. In some variations, the activation process may be similar to that described above for the working electrode.

Roughening: Furthermore, in some variations, the counter electrode surface may be electrochemically roughened in order to enhance the current-sinking or current-sourcing capacity of this electrode contingent. The electrochemical roughening process may be similar to that described above for the working electrode. Additionally or alternatively, in some variations as described above, elemental platinum metal may be deposited on the electrode to form or deposit a platinum black layer.

Anodization: Like the working and counter electrodes as described above, the reference electrode may undergo an anodization treatment using an amperometry approach in which the electrode constituent(s) assigned for the counter electrode function is subject to a fixed high anodic potential or a suitable amount of time in a moderate-strength acid solution. Exemplary parameters and other specifics of the anodization process for the counter electrode may be similar to that described above for the working electrode. Similarly, anodization for the counter electrode may Activation: Following the anodization process, the reference electrode constituents may be subjected to a cyclically scanned potential waveform in an activation process using cyclic voltammetry. In some variations, the activation process may be similar to that described above for the working electrode.

Functionalization: Following the activation process, the reference electrode constituents may be functionalized. Assuming that the reference electrode contingent of the microneedle array has undergone the aforementioned steps, a fixed anodic potential (e.g., between +0.4 and +1.0 V vs. Ag/AgCl reference electrode) may be applied for a certain suitable duration (e.g., between about 10 sec and about 10 min) in an aqueous solution. Alternatively, the reference electrode is subject to a fixed anodic potential (e.g., between about +0.4 and about +1.0 V vs. Ag/AgCl reference electrode) until a certain amount of charge has passed (e.g., between 0.01 mC and 10 mC) in an aqueous solution. In some variations, the aqueous solution may include a monomeric precursor to a conducting polymer and a charged dopant counter ion or material (e.g., poly(styrene sulfonate)) carrying an opposing charge. In this process, a thin film (e.g., between about 10 nm and about 10,000 nm) of a conducting polymer with a dispersed counter ion or material may be generated on the reference electrode surface. This creates a surface-immobilized, solid-state redox couple with a stable thermodynamic potential. In some variations, the conducting polymer may include one or more of aniline, pyrrole, acetylene, phenylene, phenylene vinylene, phenylene diamine, thiophene, 3,4-ethylenedioxythiophene, and aminophenylboronic acid.

In some alternative embodiments, a native iridium oxide film (e.g., $IrO_2$ or $Ir_2O_3$ or $IrO_4$) may be electrochemically grown on an iridium electrode surface in an oxidative process. This also creates a stable redox couple, as discussed above.

Furthermore, in some variations the reference electrode surface may be electrochemically roughened in order to enhance adhesion of the surface-immobilized redox couple. The electrochemical roughening process may be similar to that described above for the working electrode. Additionally or alternatively, in some variations as described above, elemental platinum metal may be deposited on the electrode to form or deposit a platinum black layer.

Multiple microneedles (e.g., any of the microneedle variations described herein, each of which may have a working electrode, counter electrode, or reference electrode as described above) may be arranged in a microneedle array. Considerations of how to configure the microneedles include factors such as desired insertion force for penetrating skin with the microneedle array, optimization of electrode signal levels and other performance aspects, manufacturing costs and complexity, etc.

For example, the microneedle array may include multiple microneedles that are spaced apart at a predefined pitch (distance between the center of one microneedle to the center of its nearest neighboring microneedle). In some variations, the microneedles may be spaced apart with a sufficient pitch so as to distribute force (e.g., avoid a "bed of nails" effect) that is applied to the skin of the user to cause the microneedle array to penetrate the skin. As pitch increases, force required to insert the microneedle array tends to decrease and depth of penetration tends to increase. However, it has been found that pitch only begins to affect insertion force at low values (e.g., less than about 150 μm). Accordingly, in some variations the microneedles in a microneedle array may have a pitch of at least 200 μm, at least 300 μm, at least 400 μm, at least 500 μm, at least 600 μm, at least 700 μm, or at least 750 μm. For example, the pitch may be between about 200 μm and about 800 μm, between about 300 μm and about 700 μm, or between about 400 μm and about 600 μm. In some variations, the microneedles may be arranged in a periodic grid, and the pitch may be uniform in all directions and across all regions of the microneedle array. Alternatively, the pitch may be different as measured along different axes (e.g., X, Y directions) and/or some regions of the microneedle array may include a smaller pitch while other may include a larger pitch.

Furthermore, for more consistent penetration, microneedles may be spaced equidistant from one another (e.g., same pitch in all directions). To that end, in some variations, the microneedles in a microneedle array may be arranged in a hexagonal configuration. Alternatively, the microneedles in a microneedle array may arranged in a rectangular array (e.g., square array), or in another suitable symmetrical manner Another consideration for determining configuration of a microneedle array is overall signal level provided by the microneedles. Generally, signal level at each microneedle is invariant of the total number of microneedle elements in an array. However, signal levels can be enhanced by electrically interconnecting multiple microneedles together in an array. For example, an array with a large number of electrically connected microneedles is expected to produce a greater signal intensity (and hence increased accuracy) than one with fewer microneedles. However, a higher number of microneedles on a die will increase die cost (given a constant pitch) and will also require greater force and/or velocity to insert into skin. In contrast, a lower number of microneedles on a die may reduce die cost and enable insertion into the skin with reduced application force and/or velocity. Furthermore, in some variations a lower number of microneedles on a die may reduce the overall footprint area of the die, which may lead to less unwanted localized edema and/or erythema. Accordingly, in some variations, a balance among these factors may be achieved with a microneedle array including 37 microneedles or a microneedle array including seven microneedles. However, in other variations there may be fewer microneedles in an array (e.g., between about 5 and about 35, between about 5 and about 30, between about 5 and about 25, between about 5 and about 20, between about 5 and about 15, between about 5 and about 100, between about 10 and about 30, between about 15 and about 25, etc.) or more microneedles in an array (e.g., more than 37, more than 40, more than 45, etc.).

Additionally, in some variations only a subset of the microneedles in a microneedle array may be active during operation of the analyte monitoring device. For example, a portion of the microneedles in a microneedle array may be inactive (e.g., no signals read from electrodes of inactive microneedles). In some variations, a portion of the microneedles in a microneedle array may be activated at a certain time during operation and remain active for the remainder of the operating lifetime of the device. Furthermore, in some variations, a portion of the microneedles in a microneedle array may additionally or alternatively be deactivated at a certain time during operation and remain inactive for the remainder of the operating lifetime of the device.

In considering characteristics of a die for a microneedle array, die size is a function of the number of microneedles in the microneedle array and the pitch of the microneedles. Manufacturing costs are also a consideration, as a smaller die size will contribute to lower cost since the number of dies that can be formed from a single wafer of a given area will increase. Furthermore, a smaller die size will also be less susceptible to brittle fracture due to the relative fragility of the substrate.

Furthermore, in some variations, microneedles at the periphery of the microneedle array (e.g., near the edge or boundary of the die, near the edge or boundary of the housing, near the edge or boundary of an adhesive layer on the housing, along the outer border of the microneedle array, etc.) may be found to have better performance (e.g., sensitivity) due to better penetration compared to microneedles in the center of the microneedle array or die. Accordingly, in some variations, working electrodes may be arranged largely or entirely on microneedles located at the periphery of the microneedle array, to obtain more accurate and/or precise analyte measurements.

FIG. 2 and FIG. 5 depict an illustrative schematic of 37 microneedles arranged in an example variation of a microneedle array. The 37 microneedles may, for example, be arranged in a hexagonal array with an inter-needle center-to-center pitch of about 750 μm (or between about 700 μm and about 800 μm, or between about 725 μm and about 775 μm) between the center of each microneedle and the center of its immediate neighbor in any direction.

FIG. 1 and FIG. 4 depict perspective views of an illustrative schematic of seven microneedles arranged in an example variation of a microneedle array. The seven microneedles are arranged in a hexagonal array on a substrate. The electrodes are arranged on distal portions of the microneedles extending from a first surface of the substrate. Proximal portions of the microneedles are conductively connected to respective backside electrical contacts on a second surface of the substrate opposite the first surface of the substrate. The seven microneedles may be arranged in a hexagonal array with an inter-needle center-to-center pitch of about 750 $\mu$m between the center of each microneedle and the center of its immediate neighbor in any direction. In other variations, the inter-needle center-to-center pitch may be, for example, between about 700 $\mu$m and about 800 $\mu$m, or between about 725 $\mu$m and about 775 $\mu$m. The microneedles may have an approximate outer shaft diameter of about 170 $\mu$m (or between about 150 $\mu$m and about 190 $\mu$m, or between about 125 $\mu$m and about 200 $\mu$m) and a height of about 500 $\mu$m (or between about 475 $\mu$m and about 525 $\mu$m, or between about 450 $\mu$m and about 550 $\mu$m).

Furthermore, the microneedle arrays described herein may have a high degree of configurability concerning where the working electrode(s), counter electrode(s), and reference electrode(s) are located within the microneedle array. This configurability may be facilitated by the electronics system.

The following description is an exemplary embodiment of the current subject matter.

The current invention aims to circumvent the limitations of liquid-junction reference electrodes, thereby enabling highly parallelized electrochemical sensor synthesis, via the implementation of the liquid-phase architecture in a solid-state embodiment. The said solid-state embodiment is directly integrated onto a substrate and can form an electrolytic cell when immersed in a fluid containing at least one working electrode. The current invention represents an alternative approach facilitating the synthesis of a substrate-integrated solid-state reference electrode that addresses the shortcomings of the prior art while remaining amenable to highly scalable manufacturing processes. These shortcomings include:

(1) The necessity of implementing an internal filling solution, which maintains thermodynamic redox equilibrium with a metal/metal-salt electrode immersed within, thereby yielding a stable electrical potential: (a) Limitation: An internal filling solution requires encasement in a relatively fragile glass capillary and necessitates frequent maintenance to conform within the limits of its operating specifications. This is not amenable to embodiments using conventional high-throughput manufacturing processes used in the semiconductor or microelectronics industries; (b) Mitigation: Utilization of a substrate-integrated, solid-state reference electrode containing an embedded redox couple to result in the establishment of a stable electrode potential that maintains thermodynamic redox equilibrium with the electrolytic cell.

(2) Frequent maintenance interval for conventional liquid-junction reference electrodes: (a) Limitation: Prior art liquid junction reference electrodes require frequent service intervals to conform to operating specifications. These devices often succumb to contamination or leaching of the internal filling solution, contamination or desiccation of the glass-frit semi-permeable membrane, and reduction in reference capacity over time as the metal salt dissolves into the internal filling solution. These issues are known to cause the electrode potential to become unstable and depart from the desired operating bounds. Accordingly, these reference electrodes are, oftentimes, replaced at regular intervals rather than serviced to suitable operating specifications; (b) Mitigation: A solid-state reference electrode architecture lacking a glass capillary, internal filling solution, and glass frit semi-permeable membrane would not require service intervals. As said solid-state reference electrodes would be integrated directly into a substrate contained within an analyte-selective sensor, these devices would thereby be configured for use during the synthesis of a single analyte-selective sensor rather than be subject to repeated use during processing of additional analyte-selective sensors, as in the prior art.

(3) Minimum electrolytic cell volume requirements for operating a conventional liquid-junction reference electrode: (a) Limitation: As a consequence of their three-dimensional geometry, prior art liquid junction reference electrodes require a minimum fluid volume to sustain operation, typically greater than about 200 microliters; (b) Mitigation: Substrate-integrated reference electrodes, owing to their planar geometry, are able to operate in electrolytic cells with much smaller fluid volumes, in some cases below 1 microliter (e.g. electrochemical test strips for fingerstick glucose assay).

(4) The labor-intensive assembly of conventional reference electrodes, which are multi-component in nature and not amenable to manufacturing schemes deployed in the microelectronics industry: (a) Limitation: Mechanical or hand assembly are not amenable to micro- or nano-scale electrode dimensions that are typically encountered in micro-fabricated systems; (b) Mitigation: Utilization of an electro-deposition process to deposit a conducting polymer film on a metallic electrode of nearly any geometry. The electro-deposition process is amenable to automated, scalable, and highly parallelized fabrication of highly uniform functional reference electrodes that obviate the need for mechanical/hand assembly, as is often done with conventional reference electrodes.

(5) The realization of micro-fabricated metal-salt and metal-oxide electrodes: (a) Limitation: Metal salt electrodes require chemical or electrochemical processing of an elemental metal precursor and cannot be easily synthesized, as is the case with elemental metal electrodes, using micro-manufacturing equipment; (b) Mitigation: The coating of an elemental metallic or metallic alloy electrode, trace, or pad with an overlayer containing an embedded dopant ion, which exhibits identical redox behavior to conventional metal-salt-coated metal electrodes when immersed in solution.

(6) Semi-permeable membrane junctions, which forms a half-cell: (a) Limitation: Conventional reference electrodes make extensive use of glass frit semi-permeable membranes, which facilitate electrical communication between the internal filling solution within the reference electrode and the surrounding fluid medium in which said reference electrode is immersed. The fabrication of said semi-permeable membranes employing an automated or semiconductor manufacturing process is not easily achieved owing to the inability to process the material using established micro-manufacturing techniques; (b) Mitigation: The implementation of a surface-bound redox couple emulates the semi-permeability of a conventional glass frit membrane. Said redox couple enables establishment of an ohmic connection between the underlying metal electrode and the solution in which the as-fabricated solid-state reference electrode is immersed.

(7) Inability to scale to micron- and sub-micron dimensions: (a) Limitation: Owing to their multi-component design and extensive use of materials that are incompatible with conventional micro-fabrication and semiconductor manufacturing methods, conventional reference electrodes present difficulty when attempting to scale below centimeter-scale dimensions; (b) Mitigation: Employing a fabrication/manufacturing technique and materials that are compatible with the existing circuit board manufacture and semiconductor processing infrastructure ensures that said reference electrodes can be scaled to micron- or sub-micron dimensions and integrated on substrates alongside functional electrical circuits and microelectromechanical systems.

(8) Added complexity in interfacing with controlling instrumentation: (a) Limitation: Conventional reference electrodes embody additional connectivity requirements to interface with controlling instrumentation. These connectivity requirements add complexity, require external wiring/fixturing, and use a substantial amount of space. This complexity is not desirable or efficient in high volume manufacturing; (b) Mitigation: Compatibility of said reference electrodes with existing circuit board fabrication/manufacturing techniques ensures necessary connectivity is achieved prior to introduction into batch processing.

(9) Uncontrolled reference potential drift between maintenance intervals: (a) Limitation: The target reference potential of conventional reference electrodes may drift over time as a result of contamination or leaching of the internal filling solution, contamination or desiccation of the glass-frit semipermeable membrane, or reduction in reference capacity over time between regular maintenance intervals, which could cause variability in electrodeposition or electrolysis processes; (b) Mitigation: The reference potential of said reference electrodes is dictated by the manufacturing and storage processes as the said reference electrodes would be single use.

The invention disclosed herein teaches of devices and methods to enable the electrochemical treatment of and/or electrodeposition of thin-films on working electrodes within analyte-selective sensors using a substrate-integrated reference electrode that is completely solid-state in nature. Exemplary substrates include a printed circuit board, a flex circuit, semiconductor device, or an integrated circuit and are generally sufficiently planar in geometry. The said substrate-integrated reference electrodes are realized by the deposition of thin- or thick-films on an underlying electrical conductor that facilitates ohmic contact to instrumentation configured to control the said electrodeposition process. Optionally, this approach can also function for electroplating, electrocleaning, electropolishing, anodization, and electrochemical activation processes. Methods for the deposition of said thin- or thick-films include screen printing (mesh or shadow mask stencil), spray-coating, drop casting, dip coating, aerosol deposition, vapor deposition, sputtering, electroplating, and anodic deposition. In certain embodiments, the rationale for the use of a substrate-integrated reference electrode includes the deposition of surface-immobilized layer on at least one working electrode in an electrolytic cell. A surface-immobilized layer on the at least one working electrode includes at least one of a sensing layer, a biorecognition layer, a diffusion limiting layer, a biocompatible layer, and an interference rejection layer. The surface-immobilized layer functions to impart an enhancement to the selective sensing capability of an analyte-selective sensor and requires a degree of precision in order to ensure uniformity among sensor lots in the manufacturing environment.

The invention concerns a reference electrode device configured for the electrodeposition of at least one surface-immobilized layer on at least one of a working electrode contained within body-worn analyte-selective sensor, said reference electrode device is comprised of, in order from anterior to posterior surface, a substrate, a transducer, and an overlayer. Said overlayer contains a redox couple. The said reference electrode is used as a component of an electrolytic cell and is configured to operate in the same fluid medium as the said working electrode. Said surface-immobilized layer includes at least one of a sensing layer, a biorecognition layer, a diffusion limiting layer, a biocompatible layer, and an interference rejection layer. Said working electrode is a metal (i.e. elemental platinum, palladium, rhodium, iridium, ruthenium, rhenium, gold, nickel, titanium, chromium, tungsten, tantalum), metal alloy (i.e. platinum-iridium, gold-nickel, palladium-gold), semiconductor (i.e. silicon, germanium, silicon germanium, gallium arsenide, indium gallium arsenide, gallium nitride, indium gallium nitride, indium phosphide, indium gallium phosphide), or polymer (i.e. poly(pyrrole), poly(aniline), poly(3,4-ethylenedioxythiophene)). Said analyte-selective sensor is an electrochemical sensor, a transdermal sensor, a dermal sensor, a subcutaneous sensor, or a microneedle sensor. Said substrate is a printed circuit board, flexible circuit, polymer, or semiconductor device. Said transducer is a trace, electrode, pad, via, contact point, or electrical connector and is comprised of a metal, metal alloy, or metal oxide. Said overlayer comprises at least one of a metal, metal alloy, metal oxide (i.e. $IrO_2$ or $Ir_2O_3$), metal salt (i.e. AgCl or $CuSO_4$), metal dispersion, metal ink, metal paste, semiconductor, and conducting polymer. Said redox couple is Ag/AgCl, Cu/$CuSO_4$, or $Ir_2O_3$/$IrO_2$ and facilitates the formation of a stable electrode potential between −1.5 and +1.5 Volts verses a standard hydrogen electrode. Optionally, said electrolytic cell contains at least one counter electrode. Said fluid medium is an aqueous solution, electrolytic solution (i.e. buffering agent in water), ionic liquid, solvent, or dispersion.

The invention concerns a method for the electrodeposition of at least one surface-immobilized layer on at least one of a working electrode contained within body-worn analyte-selective sensor, said method comprising, in order of execution, applying an overlayer containing a redox couple on the anterior surface of a transducer located on the surface of a substrate, thereby forming a substrate-integrated reference electrode, immersion of said substrate-integrated reference electrode in a fluid medium containing said at least one working electrode, thereby forming an electrolytic cell, and applying an electrical stimulus to said at least one working electrode wherein the application of an electrical stimulus effects the electrodeposition of said surface-immobilized layer on at least one of a working electrode contained within a body-worn analyte-selective sensor. Said surface-immobilized layer includes at least one of a sensing layer, a biorecognition layer, a diffusion limiting layer, a biocompatible layer, and an interference rejection layer. Said working electrode is a metal (i.e. elemental platinum, palladium, rhodium, iridium, ruthenium, rhenium, gold, nickel, titanium, chromium, tungsten, tantalum), metal alloy (i.e. platinum-iridium, gold-nickel, palladium-gold), semiconductor (i.e. silicon, germanium, silicon germanium, gallium arsenide, indium gallium arsenide, gallium nitride, indium gallium nitride, indium phosphide, indium gallium phosphide), or polymer (i.e. poly(pyrrole), poly(aniline), poly(3,4-ethylenedioxythiophene)). Said analyte-selective sensor is an electrochemical sensor, a transdermal sensor, a dermal sensor, a subcutaneous sensor, or a microneedle sensor. Said overlayer comprises at least one of a metal, metal alloy, metal oxide (i.e. $IrO_2$ or $Ir_2O_3$), metal salt (i.e. AgCl or $CuSO_4$), metal dispersion, metal ink, metal paste, semiconductor, and conducting polymer. Said redox couple is Ag/AgCl, Cu/$CuSO_4$, or $Ir_2O_3$/$IrO_2$ and facilitates the formation of a stable electrode potential between −1.5 and +1.5 Volts verses a standard hydrogen electrode. Optionally, said electrolytic cell contains at least one counter electrode. Said fluid medium is an aqueous solution, electrolytic solution (i.e. buffering agent in water), ionic liquid, solvent, or dispersion. Said electrical stimulus is at least one of a DC voltage, a DC current, an AC voltage, an AC current, a specified quantity of electrical charge, an electrical function, and an electrical waveform.

In alternative embodiments, the invention concerns a method for sustaining an electrochemical reaction on at least one of a working electrode contained within body-worn analyte-selective sensor, said method comprising, in order of execution, applying an overlayer containing a redox couple on the anterior surface of a transducer located on the surface of a substrate, thereby forming a substrate-integrated reference electrode, immersion of said substrate-integrated reference electrode in a solution containing said least one working electrode, and applying an electrical stimulus to said at least one working electrode wherein the application of an electrical stimulus effects the electrochemical reaction on said at least one of a working electrode contained within a body-worn analyte-selective sensor. Said surface-immobilized layer includes at least one of a sensing layer, a biorecognition layer, a diffusion limiting layer, a biocompatible layer, and an interference rejection layer. Said working electrode is a metal (i.e. elemental platinum, palladium, rhodium, iridium, ruthenium, rhenium, gold, nickel, titanium, chromium, tungsten, tantalum), metal alloy (i.e. platinum-iridium, gold-nickel, palladium-gold), semiconductor (i.e. silicon, germanium, silicon germanium, gallium arsenide, indium gallium arsenide, gallium nitride, indium gallium nitride, indium phosphide, indium gallium phosphide), or polymer (i.e. poly(pyrrole), poly(aniline), poly(3, 4-ethylenedioxythiophene)). Said analyte-selective sensor is an electrochemical sensor, a transdermal sensor, a dermal sensor, a subcutaneous sensor, or a microneedle sensor. Said overlayer comprises at least one of a metal, metal alloy, metal oxide (i.e. $IrO_2$ or $Ir_2O_3$), metal salt (i.e. AgCl or $CuSO_4$), metal dispersion, metal ink, metal paste, semiconductor, and conducting polymer. Said redox couple is Ag/AgCl, $Cu/CuSO_4$, or $Ir_2O_3/IrO_2$ and facilitates the formation of a stable electrode potential between −1.5 and +1.5 Volts verses a standard hydrogen electrode.

Optionally, said electrolytic cell contains at least one counter electrode. Said fluid medium is an aqueous solution, electrolytic solution (i.e. buffering agent in water), ionic liquid, solvent, or dispersion. Said electrical stimulus is at least one of a DC voltage, a DC current, an AC voltage, an AC current, a specified quantity of electrical charge, an electrical function, and an electrical waveform.

The device preferably comprises a substrate, a transducer, an overlayer, an electrolytic cell, and a working electrode. The substrate provides support for substrate-integrated reference electrode. Also may assist in containment of fluid in electrolytic cell. SUBSTRATE can comprise a printed circuit board, flexible circuit, polymer, or semiconductor device. The transducer serves as the intermediary between an electrical circuit (i.e. potentiostat, galvanostat) and substrate-integrated reference electrode. Said TRANSDUCER can comprise a trace, electrode, pad, via, contact point, or electrical connector. Said TRANSDUCER can comprise a metal, metal alloy, or metal oxide. The overlayer hosts a stable redox couple with a known and stable electrode potential. Said OVERLAYER comprises at least one of a metal, metal alloy, metal oxide (i.e. $IrO_2$ or $Ir_2O_3$), metal salt (i.e. AgCl), metal dispersion, metal ink, metal paste, semiconductor, and conducting polymer. The electrolytic cell is a closed volume containing a fluid comprising at least one of water, a solvent, a salt, a monomer, a metal ion, and a deposition solution. At a minimum, said CELL requires at least one working electrode and at least one reference electrode. Optionally, CELL can incorporate at least one counter electrode. A surface-immobilized layer is electrode-posited on at least one ELECTRODE in a CELL to impart a selective analyte sensing capability. Said ELECTRODE is contained within a body-worn analyte-selective sensor. Said surface-immobilized layer includes at least one of a sensing layer, a biorecognition layer, a diffusion limiting layer, a biocompatible layer, and an interference rejection layer. Said electrode is comprised is a metal, metal alloy, semiconductor, or polymer. Said metal is elemental platinum, palladium, rhodium, iridium, ruthenium, rhenium, gold, nickel, titanium, chromium, tungsten, or tantalum. Said semiconductor is silicon, germanium, silicon germanium, gallium arsenide, indium gallium arsenide, gallium nitride, indium gallium nitride, indium phosphide, and indium gallium phosphide. Said analyte-selective sensor is an electrochemical sensor, a transdermal sensor, a dermal sensor, a subcutaneous sensor, or a microneedle sensor.

Said stable electrode potential is between −1.5 and +1.5 Volts verses a standard hydrogen electrode.

A first step of the method is Applying OVERLAYER on anterior surface of TRANSDUCER located on SUBSTRATE, thereby forming a substrate-integrated reference electrode, wherein said OVERLAYER comprises at least one of a metal, metal alloy, metal oxide, metal salt, metal dispersion, metal ink, metal paste, semiconductor, and conducting polymer. Said OVERLAYER contains an embedded redox couple with a stable and well-known electrode potential. Said TRANSDUCER is a trace, electrode, pad, via, contact point, or electrical connector. Said TRANSDUCER comprises a metal, metal alloy, or metal oxide. Said SUBSTRATE is comprised of a printed circuit board, flexible circuit, polymer, or semiconductor device.

A second step of the method is immersion of said substrate-integrated reference electrode in a solution containing said least one ELECTRODE, thereby forming a CELL and enabling fluidic contact between the at least one ELECTRODE and substrate-integrated reference electrode. Said CELL comprises at least one of water, a solvent, a salt, an ionic liquid, a monomer, a metal ion, and a deposition solution.

A third step of the method is applying an electrical stimulus to said at least one ELECTRODE, which effects the deposition of a surface-immobilized layer on at least one of an ELECTRODE contained within a body-worn analyte-selective sensor. Said electrical stimulus can include either a voltage or current. Said electrical stimulus can comprise at most one of the following techniques: amperometry, chronoamperometry, coulometry, voltammetry, cyclic voltammetry, linear sweep voltammetry, a galvanic electrochemical method, and a potentiometric electrochemical method.

An input of the invention is a substrate-integrated reference electrode, which is an electrode containing a redox couple with a stable and well-known electrode potential on the anterior surface of a sufficiently planar substrate. Said stable electrode potential is between −1.5 and +1.5 Volts verses a standard hydrogen electrode. Said substrate is a printed circuit board, flexible circuit, polymer, or semiconductor device.

An output of the invention is deposition of a surface-immobilized layer on at least one of a working electrode contained within a body-worn analyte-selective sensor, which is a functional layer, membrane, or film containing at least one of a sensing layer, a biorecognition layer, a diffusion limiting layer, a biocompatible layer, and an interference rejection layer.

The device preferably comprises a substrate, a transducer, and a working electrode. An overlayer comprises a layer deposited on the surface of the transducer. An electrolytic cell is formed by means of immersion of the reference and working electrodes in a fluid medium.

The components of a complete electrolytic cell featuring a substrate-integrated reference electrode for the deposition of a surface-immobilized layer on at least one working electrode include: the electrolytic cell is positioned on the substrate, with a transducer, a working electrode, an overlay with an embedded redox couple and a surface immobilized layer.

Exemplary Embodiments

Embodiment I-1. A device, comprising:
a substrate;
a reference electrode comprising
a transducer positioned on an anterior surface of the substrate; and
an overlay comprising a redox couple applied to a first surface of the transducer; and
a working electrode positioned on the anterior surface of the substrate;
wherein the reference electrode and the working electrode form an electrolytic cell in a fluid medium;
wherein application of an electrical stimulus to the working electrode in the electrolytic cell provides electrodeposition of a surface layer on the working electrode.

Embodiment I-2. The device of embodiment I-1, wherein the working electrode is a sensing element in an analyte-selective sensor.

Embodiment I-3. The device of embodiment I-1, wherein the surface layer comprises at least one selected from the group of a sensing layer, a biorecognition layer, a diffusion limiting layer, a biocompatible layer, and an interference rejection layer.

Embodiment I-4. The device of embodiment I-1, wherein the working electrode comprises at least one selected from the group of a metal, a metal alloy, a semiconductor, and a polymer.

Embodiment I-5. The device of embodiment I-1, wherein the substrate comprises at least one selected from the group of a printed circuit board, a flexible circuit, a polymer, and a semiconductor device.

Embodiment I-6. The device of embodiment I-1, wherein the transducer comprises at least one selected from the group of a trace, an electrode, a pad, a via, a contact point, and an electrical connector.

Embodiment I-7. The device of embodiment I-1, wherein the transducer comprises at least one selected from the group of a metal, a metal alloy, and a metal oxide.

Embodiment I-8. The device of embodiment I-1, wherein the overlayer comprises at least one selected from the group of a metal, a metal alloy, a metal oxide, a metal salt, a metal dispersion, a metal ink, a metal paste, a semiconductor, and a conducting polymer.

Embodiment I-9. The device of embodiment I-1, wherein the redox couple comprises Ag/AgCl, Cu/CuSO$_4$, or Ir$_2$O$_3$/IrO$_2$.

Embodiment I-10. The device of embodiment I-1, wherein said redox couple facilitates the formation of a stable electrode potential.

Embodiment I-11. The device of embodiment I-10, wherein the stable electrode potential is between −1.5 volts and +1.5 volts versus a standard hydrogen electrode.

Embodiment I-12. The device of embodiment I-1, wherein the application of the electrical stimulus comprises one or more selected from the group of amperometry, chronoamperometry, coulometry, voltammetry, cyclic voltammetry, linear sweep voltammetry, a galvanic electrochemical application, and a potentiometric electrochemical application.

Embodiment I-13. The device of embodiment I-1, wherein said electrolytic cell comprises a counter electrode.

Embodiment I-14. The device of embodiment I-1, wherein the fluid medium comprises at least one selected from the group of an aqueous solution, an electrolytic solution, an ionic liquid, a solvent, or a dispersion.

Embodiment I-15. A method, comprising:
providing a device comprising a substrate, a reference electrode, and a working electrode, wherein the reference electrode and the working electrode are positioned on an anterior surface of the substrate and form an electrolytic cell in a fluid medium, and wherein the reference electrode comprises a transducer positioned on the anterior surface of the substrate and an overlay comprising a redox couple applied to a first surface of the transducer;
immersing the substrate in a fluid medium; and
applying an electrical stimulus to the working electrode, thereby causing electrodeposition of a surface layer on the working electrode.

Embodiment I-16. The method of embodiment I-15, wherein the working electrode is configured to function as a sensing element in an analyte-selective sensor.

Embodiment I-17. The method of embodiment I-15, wherein the surface layer comprises at least one selected from the group of a sensing layer, a biorecognition layer, a diffusion limiting layer, a biocompatible layer, and an interference rejection layer.

Embodiment I-18. The method of embodiment I-15, wherein the working electrode comprises at least one selected from the group of a metal, a metal alloy, a semiconductor, and a polymer.

Embodiment I-19. The method of embodiment I-15, wherein the substrate comprises at least one selected from the group of a printed circuit board, a flexible circuit, a polymer, and a semiconductor device.

Embodiment I-20. The method of embodiment I-15, wherein the transducer comprises at least one selected from the group of a trace, an electrode, a pad, a via, a contact point, and an electrical connector.

Embodiment I-21. The method of embodiment I-15, wherein the transducer comprises at least one selected from the group of a metal, a metal alloy, and a metal oxide.

Embodiment I-22. The method of embodiment I-15, wherein the overlayer comprises at least one selected from the group of a metal, a metal alloy, a metal oxide, a metal salt, a metal dispersion, a metal ink, a metal paste, a semiconductor, and a conducting polymer.

Embodiment I-23. The method of embodiment I-15, wherein the redox couple comprises Ag/AgCl, Cu/CuSO$_4$, or Ir$_2$O$_3$/IrO$_2$.

Embodiment I-24. The method of embodiment I-15, wherein said redox couple facilitates the formation of a stable electrode potential.

Embodiment I-25. The method of embodiment I-24, wherein the stable electrode potential is between −1.5 volts and +1.5 volts versus a standard hydrogen electrode.

Embodiment I-26. The method of embodiment I-15, wherein the application of the electrical stimulus comprises one or more selected from the group of amperometry, chronoamperometry, coulometry, voltammetry, cyclic voltammetry, linear sweep voltammetry, a galvanic electrochemical application, and a potentiometric electrochemical application.

Embodiment I-27. The method of embodiment I-15, wherein said electrolytic cell comprises a counter electrode.

Embodiment I-28. The method of embodiment I-15, wherein the fluid medium comprises at least one selected from the group of an aqueous solution, an electrolytic solution, an ionic liquid, a solvent, and a dispersion.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method, comprising:
providing a device comprising a substrate, a planar reference electrode positioned only on an anterior surface of the substrate, and a working electrode positioned on a microneedle extending from the anterior surface of the substrate, wherein the planar reference electrode and the working electrode form an electrolytic cell in a fluid medium, and wherein the planar reference electrode comprises a transducer positioned on the anterior surface of the substrate and an overlay comprising a redox couple applied to a first surface of the transducer;
immersing the device in the fluid medium; and
applying an electrical stimulus to the working electrode, thereby causing electrodeposition of a surface layer on the working electrode.

2. The method of claim 1, wherein the working electrode is configured to function as a sensing element in an analyte-selective sensor.

3. The method of claim 1, wherein the surface layer comprises at least one of a sensing layer, a biorecognition layer, a diffusion limiting layer, a biocompatible layer, or an interference rejection layer.

4. The method of claim 1, wherein the working electrode comprises at least one of a metal, a metal alloy, a semiconductor, or a polymer.

5. The method of claim 1, wherein the substrate comprises at least one of a printed circuit board, a flexible circuit, a polymer, or a semiconductor.

6. The method of claim 1, wherein the transducer comprises at least one of a trace, an electrode, a pad, a via, a contact point, or an electrical connector.

7. The method of claim 1, wherein the transducer comprises at least one of a metal, a metal alloy, or a metal oxide.

8. The method of claim 1, wherein the overlay comprises at least one of a metal, a metal alloy, a metal oxide, a metal salt, a metal dispersion, a metal ink, a metal paste, a semiconductor, or a conducting polymer.

9. The method of claim 1, wherein the redox couple comprises Ag/AgCl, Cu/CuSO$_4$, or Ir$_2$O$_3$/IrO$_2$.

10. The method of claim 1, wherein said redox couple facilitates the formation of a stable electrode potential.

11. The method of claim 10, wherein the stable electrode potential is between −1.5 volts and +1.5 volts versus a standard hydrogen electrode.

12. The method of claim 1, wherein the application of the electrical stimulus comprises one or more of amperometry, chronoamperometry, coulometry, voltammetry, cyclic voltammetry, linear sweep voltammetry, a galvanic electrochemical application, or a potentiometric electrochemical application.

13. The method of claim 1, wherein said electrolytic cell comprises a counter electrode.

14. The method of claim 1, wherein the fluid medium comprises at least one of an aqueous solution, an electrolytic solution, an ionic liquid, a solvent, or a dispersion.

15. A method, comprising:
providing a device comprising a semiconductor substrate, a reference electrode positioned on an anterior surface of the semiconductor substrate, and a working electrode positioned on a microneedle extending from the anterior surface of the semiconductor substrate, wherein the reference electrode and the working electrode form an electrolytic cell in a fluid medium, and wherein the reference electrode comprises a transducer positioned on the anterior surface of the semiconductor substrate and an overlay comprising a redox couple applied to a first surface of the transducer;
immersing the device in the fluid medium; and
applying an electrical stimulus to the working electrode, thereby causing electrodeposition of a surface layer on the working electrode.

16. The method of claim 15, wherein the working electrode is configured to function as a sensing element in an analyte-selective sensor.

17. The method of claim 15, wherein the surface layer comprises at least one of a sensing layer, a biorecognition layer, a diffusion limiting layer, a biocompatible layer, or an interference rejection layer.

18. The method of claim 15, wherein the working electrode comprises at least one of a metal, a metal alloy, a semiconductor, or a polymer.

19. The method of claim 15, wherein the transducer comprises at least one of a trace, an electrode, a pad, a via, a contact point, or an electrical connector.

20. The method of claim 15, wherein the transducer comprises at least one of a metal, a metal alloy, or a metal oxide.

21. The method of claim 15, wherein the overlay comprises at least one of a metal, a metal alloy, a metal oxide, a metal salt, a metal dispersion, a metal ink, a metal paste, a semiconductor, or a conducting polymer.

22. The method of claim 15, wherein the redox couple comprises Ag/AgCl, Cu/CuSO$_4$, or Ir$_2$O$_3$/IrO$_2$.

23. The method of claim 15, wherein said redox couple facilitates the formation of a stable electrode potential.

24. The method of claim 23, wherein the stable electrode potential is between −1.5 volts and +1.5 volts versus a standard hydrogen electrode.

25. The method of claim 15, wherein the application of the electrical stimulus comprises one or more of amperometry, chronoamperometry, coulometry, voltammetry, cyclic voltammetry, linear sweep voltammetry, a galvanic electrochemical application, or a potentiometric electrochemical application.

26. The method of claim 15, wherein said electrolytic cell comprises a counter electrode.

27. The method of claim 15, wherein the fluid medium comprises at least one of an aqueous solution, an electrolytic solution, an ionic liquid, a solvent, or a dispersion.

* * * * *